United States Patent
Shin et al.

(10) Patent No.: US 9,777,301 B2
(45) Date of Patent: Oct. 3, 2017

(54) METHOD FOR PRODUCING OPTICALLY ACTIVE AMINE COMPOUNDS BY DERACEMIZATION

(71) Applicant: INDUSTRY-ACADEMIC COOPERATION FOUNDATION, YONSEI UNIVERSITY, Seoul (KR)

(72) Inventors: Jong-Shik Shin, Gyeonggi-do (KR); Eul-Soo Park, Gyeonggi-do (KR); M. Shaheer Malik, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/352,269

(22) PCT Filed: Dec. 13, 2013

(86) PCT No.: PCT/KR2013/011574
§ 371 (c)(1),
(2) Date: May 18, 2016

(87) PCT Pub. No.: WO2014/092496
PCT Pub. Date: Jun. 19, 2014

(65) Prior Publication Data
US 2016/0289715 A1    Oct. 6, 2016

(30) Foreign Application Priority Data

Dec. 13, 2012 (KR) .......................... 10-2012-0145526
Dec. 13, 2012 (KR) .......................... 10-2012-0145528

(51) Int. Cl.
C12P 13/00    (2006.01)
C12P 41/00    (2006.01)
C12P 13/06    (2006.01)

(52) U.S. Cl.
CPC ............. *C12P 13/001* (2013.01); *C12P 13/06* (2013.01); *C12P 41/007* (2013.01)

(58) Field of Classification Search
CPC ........ C12P 13/001; C12P 13/06; C12P 41/007
See application file for complete search history.

(56) References Cited

U.S. PATENT DOCUMENTS 6,358,714 B1 * 3/2002 Fotheringham ...... C12N 9/1096
                                                                            435/106
8,841,096 B2 * 9/2014 Sieber .................. C07D 493/04
                                                                             435/119

(Continued)

FOREIGN PATENT DOCUMENTS

KR    1020030072067      9/2003
KR    1012915860000      7/2013

OTHER PUBLICATIONS

Cho et al. Biotech. Bioengin. (2003) 81 (7) 783-789.*

*Primary Examiner* — Alexander Kim
(74) *Attorney, Agent, or Firm* — Duane Morris LLP; Gregory M. Lefkowitz; Jason M. Nolan

(57) ABSTRACT

Disclosed are methods for producing optically active amino acids and amines. According to the methods, α-keto acids are generated as reaction intermediates, and as a result, ω-transaminase-catalyzed kinetic resolution of racemic amino acids or amines as racemic amine compounds enables the production of optically active amine compounds without the need to use expensive α-keto acids as starting materials. Therefore, the optically active amine compounds are produced at greatly reduced costs. In addition, the optically active amine compounds have high enantiomeric excess.

10 Claims, 3 Drawing Sheets

(56) References Cited

U.S. PATENT DOCUMENTS

2009/0209012 A1\* 8/2009 Hayashi ............... C12N 9/0014
　　　　　　　　　　　　　　　　　　　　　435/115
2009/0246837 A1　10/2009 Robins et al.
2013/0029386 A1　 1/2013 Liao et al.

\* cited by examiner

METHOD FOR PRODUCING OPTICALLY ACTIVE AMINE COMPOUNDS BY DERACEMIZATION

CROSS-REFERENCE TO RELATED APPLICATIONS

This application is a §371 national stage entry of International Application No. PCT/KR2013/011574, filed Dec. 13, 2013, which claims priority to South Korean Patent Application No. 10-2012-0145526 filed Dec. 13, 2012 and South Korean Patent Application No. 10-2012-0145528 filed Dec. 13, 2012, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 12, 2013, is named G1035-01001_seq1.txt and is 30,704 bytes in size.

BACKGROUND OF THE INVENTION

1. Field of the Invention

The present invention relates to methods for producing optically active amine compounds using ω-transaminases, and more specifically to methods for resolving racemic amines or amino acids into optically active amines or amino acids using ω-transaminases as biocatalysts.

2. Description of the Related Art

Chiral molecules are like left and right hands, which are not superimposable on their mirror images. The word "chiral" comes from the Greek word "chir-" for hand. Chiral compounds are optically active (that means they have the ability to rotate polarized light). In such a sense, a drug whose two molecules exist as enantiomers because of their three-dimensional structures, which cannot be superimposed onto each other, is considered as a "chiral pharmaceutical drug." Production of optically pure chiral compounds has attracted growing attention. Particularly, chiral amines or chiral amino acids play vital roles in the pharmaceutical, agrochemical, and chemical industries.

Chiral amines are used as indispensable building blocks for a number of pharmaceutical drugs including (S)-rivastigmine for treatment of Alzheimer's disease, dilevalol as an antihypertensive drug, sitagliptin as an antidiabetic drug and mexiletine as an antiarrhythmic and antimyotonic drug. Owing to the pharmaceutical importance of the chiral amines, biocatalytic approaches to produce the optically active chiral amines such as kinetic resolution, asymmetric synthesis, and deracemization have been extensively studied for developing greener alternatives to chemical processes including preferential crystallization and asymmetric catalytic hydrogenation.

Chiral amino acids are also important compounds in diverse sectors, including pharmaceutical, food, agricultural, and chemical industries. Natural amino acids can be produced by simple processes such as fermentation, while the production of unnatural amino acids by fermentation has not been well established and is thus dependent on the use of biocatalysts or chemical catalysts. Chemical catalysts for the production of unnatural amino acids are very expensive, which is a cause of high costs in the production of unnatural amino acids. Accordingly, biocatalysts are usually employed to produce unnatural amino acids.

ω-transaminase displays high turnover rate, stringent enantioselectivity, high stability and no requirement of external cofactor regeneration. Due to these advantages, ω-transaminase has attracted considerable attention as effective biocatalysts for the production of chiral compounds. Particularly, methods for producing optically active amines or amino acids have emerged that include providing an α-keto acid as an amino acceptor substrate, together with ω-transaminase, and kinetically resolving a racemic compound for deracemization. The reasons for the use of the α-keto acid as an amino acceptor are low enantiomeric excess, severe enzyme inactivation, and chemical toxicity of conventional cheap amino acceptors such as propanal and butanol. The α-keto acid is free from such problems but its high cost inevitably leads to an increase in the production cost of the final optically active compounds. In an attempt to produce an optically active compound at reduced cost, Korean Patent Registration No. 10-1291586 reports the use of a fusion protein of vitreoscilla hemoglobin and D-amino acid oxidase. The application of this method is, however, limited to the resolution of homoalanine.

SUMMARY OF THE INVENTION

The present invention has been made in an effort to solve the above problems, and it is an object of the present invention to provide methods for producing optically active amine compounds from racemic amine compounds. It is a more specific object of the present invention to provide methods for producing optically active amine compounds with high enantiomeric excess from racemic amine compounds at reduced costs in which α-keto acids are generated as intermediates and are used as substrates for ω-transaminase, eliminating the need to use expensive α-keto acids as starting materials.

According to one aspect of the present invention, there is provided a method for producing an optically active amino acid, including 1) providing a racemic amino acid, an amino acceptor, and an amino donor as substrates to a D- or L-amino acid transaminase and an (S)- or (R)-selective ω-transaminase as enzymes, 2) reacting the racemic amino acid substrate and the amino acceptor substrate provided in step 1) with the D- or L-amino acid transaminase to generate an α-keto acid, and 3) reacting the α-keto acid with the (S)- or (R)-selective ω-transaminase to produce an optically active amino acid.

According to another aspect of the present invention, there is provided a method for producing an optically active amine, including 1) providing a racemic amine and L-threonine as substrates to a threonine deaminase and an (S)- or (R)-selective transaminase as enzymes, 2) deaminating the L-threonine by the threonine deaminase to generate an α-keto acid as an amino acceptor, and 3) kinetically resolving the racemic amine provided in step 1) and the α-keto acid generated in step 2) by the (S)- or (R)-selective ω-transaminase to produce an optically active amine.

According to one embodiment of the present invention, the (S)-selective ω-transaminase may be an enzyme derived from *Ochrobactrum anthropi* and encoded by a base sequence set forth in SEQ ID NO: 1 or an enzyme derived from *Paracoccus denitrificans* and encoded by a base sequence set forth in SEQ ID NO: 2.

The (R)-selective ω-transaminase may be an enzyme derived from *Aspergillus terreus* and encoded by a base sequence set forth in SEQ ID NO: 3 or an enzyme derived from *Arthrobacter* sp. and encoded by a base sequence set forth in SEQ ID NO: 4.

The racemic amino acid may be selected from the group consisting of racemic alanine, racemic serine, racemic homoserine, racemic norvaline, racemic norleucine, racemic leucine, and mixtures thereof.

The racemic amine may be selected from the group consisting of α-methylbenzylamine, 4-fluoro-α-methylbenzylamine, α-ethylbenzylamine, 1-methyl-3-phenylpropylamine, 1-aminoindane, sec-butylamine, cyclopropylethylamine, 2-aminopentane, 2-aminooctane, 1-methoxy-2-propylamine, alaninol, and mixtures thereof.

The present invention also provides an optically active amino acid or an optically active amine produced by the corresponding method.

According to the methods of the present invention, optically active amines and amino acids as optically active amine compounds can be produced at greatly reduced costs without the need to provide expensive α-keto acids as substrates, which have been used in conventional methods for producing optically active compounds using ω-transaminases.

The final optically active amine compounds produced by the methods can be used in pharmaceutical drugs and agrochemicals due to their high enantiomeric excess.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
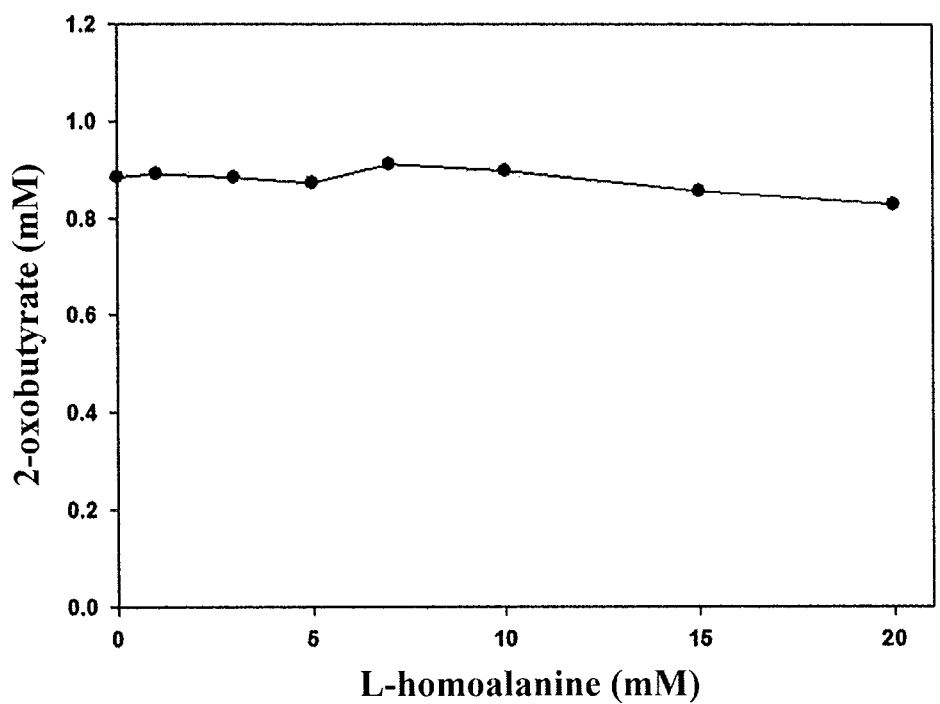
FIG. 1 is a graph showing the inactivation of a D-amino acid transaminase toward L-amino acid.

The present inventors have earnestly conducted research to develop methods for producing optically active amine compounds at reduced costs and as a result found that asymmetric, optically active amine compounds can be produced by deracemization. The present invention has been accomplished based on the finding.

Generally, resolution of optically pure amine compounds from racemic amine compounds can be performed by suitable methods such as kinetic resolution, asymmetric synthesis, and deracemization. Particularly, the production of an optically pure amine compound via deracemization can be achieved by deracemizing a racemic amine compound as a substrate and reacting the deracemized substrate with an α-keto acid and an (S)- or (R)-selective ω-transaminase. The present invention is directed to methods for producing optically active amine compounds with high purity at reduced costs by generating α-keto acids as intermediate without the need to provide expensive α-keto acids as substrates, which are currently used for the optical resolution of racemic amine compounds. The racemic amine compounds may be racemic amines or amino acids. Optically active amine compounds produced by the methods of the present invention may be amino acid and amine compounds with high enantiomeric excess.

Specifically, the present invention provides a method for producing an L-amino acid, including 1) providing a racemic amino acid, an amino acceptor, and an amino donor as substrates to a D-amino acid transaminase and an (S)-selective ω-transaminase as enzymes, 2) reacting the racemic amino acid substrate and the amino acceptor substrate provided in step 1) with the D-amino acid transaminase to generate an α-keto acid, and 3) reacting the α-keto acid with the (S)-selective ω-transaminase to produce an optically active L-amino acid.

According to the method of the present invention, the L-amino acid may be produced via Reaction Scheme 1:

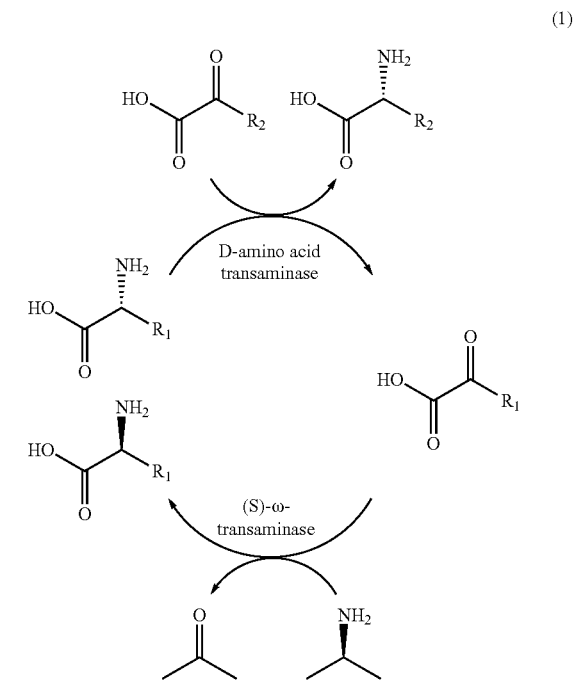

(1)

wherein each $R_1$ is independently selected from the group consisting of methyl, ethyl, propyl, butyl, hydroxymethyl, hydroxyethyl, 2-methylpropyl and combinations thereof, and each $R_2$ may be 2-carboxyethyl, phenyl or phenylmethyl.

As depicted in Reaction Scheme 1, the D-amino acid of the racemic amino acid serves as a substrate for the D-amino acid transaminase, the amino group of the D-amino acid is transferred to the amino acceptor by the action of the D-amino acid transaminase, and as a result, the α-keto acid can be generated as an intermediate. The intermediate α-keto acid receives the amino group from the amino donor by the action of the (S)-selective ω-transaminase to produce the desired L-amino acid as a final product. That is, deracemization of the racemic amino acid by the action of the D-amino acid transaminase and the (S)-selective ω-transaminase gives the pure L-amino acid.

Specifically, the present invention also provides a method for producing a D-amino acid, including 1) providing a racemic amino acid, an amino acceptor, and an amino donor as substrates to an L-amino acid transaminase and an (R)-selective ω-transaminase as enzymes, 2) reacting the racemic amino acid substrate and the amino acceptor substrate provided in step 1) with the L-amino acid transaminase to generate an α-keto acid, and 3) reacting the α-keto acid with the (R)-selective ω-transaminase to produce an optically active D-amino acid.

According to the method of the present invention, the D-amino acid may be produced via Reaction Scheme 2;

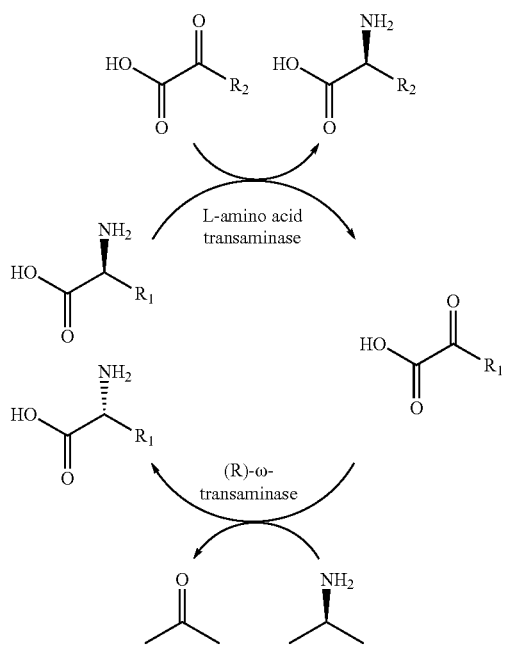

(2)

wherein each $R_1$ is independently selected from the group consisting of methyl, ethyl, propyl, butyl, hydroxymethyl, hydroxyethyl and combinations thereof, and each $R_2$ may be 2-carboxyethyl, phenyl or phenylmethyl.

As depicted in Reaction Scheme 2, the L-amino acid of the racemic amino acid serves as a substrate for the L-amino acid transaminase, the amino group of the L-amino acid is transferred to the amino acceptor by the action of the L-amino acid transaminase, and as a result, the α-keto acid can be generated as an intermediate. The intermediate α-keto acid receives the amino group from the amino donor by the action of the (R)-selective ω-transaminase to produce the desired D-amino acid as a final product. That is, the coupled enzyme reactions of the L-amino acid transaminase and the (R)-selective ω-transaminase give the pure D-amino acid.

As depicted in Reaction Scheme 1 or 2, the α-keto acid is not provided as a substrate and is generated as an intermediate. The D-amino acid transaminase is selective for the D-amino acid of the racemic amino acid or the L-amino acid transaminase is selective for the L-amino acid of the racemic amino acid. Due to this selectivity, the amino group of the selected amino acid is transferred to the amino acceptor to generate the α-keto acid.

In Reaction Scheme 1, the L-amino acid of the racemic amino acid does not participate in the reaction and only the D-amino acid of the racemic amino acid is isomerized to the L-amino acid as its enantiomer. As a result of this enantiomeric isomerization, the L-amino acid is optically resolved from the racemic amino acid. Likewise, in Reaction Scheme 2, the D-amino acid of the racemic amino acid does not participate in the reaction and only the L-amino acid of the racemic amino acid is isomerized to the D-amino acid as an enantiomer. As a result of this enantiomeric isomerization, the D-amino acid is optically resolved from the racemic amino acid. The enantiomeric excess (ee) values of the optically active amino acids resolved from the racemic amino acids by the methods of the present invention may be 99% or greater.

As depicted in Reaction Scheme 1, the reaction product of the amino acceptor and the amino group of the amino acid, together with the product L-amino acid, remains as a final product without participating in the subsequent reaction. The reaction product may be D-glutamate, D-phenylglycine or D-phenylalanine. The amino donor loses its amino group by the action of the ω-transaminase to generate the ketone, which may also remain as a final product.

As depicted in Reaction Scheme 2, the reaction product of the amino acceptor and the amino group of the amino acid, together with the product D-amino acid, remains as a final product without participating in the subsequent reaction. The reaction product may be L-glutamate, L-phenylglycine or L-phenylalanine. The amino donor loses its amino group by the action of the ω-transaminase to generate the ketone, which may also remain as a final product.

The optically active amino acids as the final products produced by the methods of the present invention are preferably selected from the group consisting of optically active D- and L-configurations of alanine, homoalanine, serine, homoserine, norvaline, norleucine, and leucine.

The racemic amino acid as one of the substrates provided in step 1) is not particularly limited so long as it possesses activity toward the D- or L-amino acid transaminase and the (S)- or (R)-selective ω-transaminase. The racemic amino acid is preferably selected from the group consisting of alanine, serine, homoserine, norvaline, norleucine, leucine, and mixtures thereof.

The amino acceptor as one of the substrates provided in step 1) should possess activity toward the D- or L-amino acid transaminase but be inactive toward the (S)- or (R)-selective ω-transaminase. α-ketoglutarate, phenylglyoxylate, and phenylpyruvate that have no activity toward the ω-transaminase may be provided as preferable amino acceptors for the reactions in the methods of the present invention.

The amino donor as one of the substrates provided in step 1) should be inactive toward the D- or L-amino acid transaminase but should provide an amino group while being active toward the (S)- or (R)-selective ω-transaminase. The amino donor is preferably selected from the group consisting of isopropylamine, methylbenzylamine, benzylamine, and mixtures thereof.

Any D-amino acid transaminase may be used without particular limitation so long as it actively reacts with the amino acceptor while enabling deracemization of the racemic amino acid. An enzyme derived from *Bacillus sphaericus* and encoded by a base sequence set forth in SEQ ID NO: 5 is preferably used as the D-amino acid transaminase.

Any L-amino acid transaminase may be used without particular limitation so long as it actively reacts with the amino acceptor while enabling deracemization of the racemic amino acid. An enzyme derived from *Escherichia coli* and encoded by a base sequence set forth in SEQ ID NO: 6 is preferably used as the L-amino acid transaminase.

The (S)-selective ω-transaminase is not particularly limited so long as it can react with the α-keto acid to produce the L-amino acid. An enzyme derived from *Ochrobactrum anthropi* and encoded by a base sequence set forth in SEQ ID NO: 1 or an enzyme derived from *Paracoccus denitrificans* and encoded by a base sequence set forth in SEQ ID NO: 2 is preferably used as the (S)-selective ω-transaminase.

The (R)-selective ω-transaminase is not particularly limited so long as it can react with the α-keto acid to produce the D-amino acid. An enzyme derived from *Aspergillus terreus* and encoded by a base sequence set forth in SEQ ID NO: 3 or an enzyme derived from *Arthrobacter* sp. and encoded by a base sequence set forth in SEQ ID NO: 4 is preferably used as the (R)-selective ω-transaminase.

Specifically, the present invention also provides a method for producing an optically active amine, including 1) providing a racemic amine and L-threonine as substrates to a threonine deaminase and an (S)- or (R)-selective ω-transaminase as enzymes, 2) deaminating the L-threonine by the threonine deaminase to generate an α-keto acid as an amino acceptor, and 3) kinetically resolving the racemic amine provided in step 1) and the α-keto acid generated in step 2) by the (S)- or (R)-selective ω-transaminase to produce an optically active amine.

According to the method of the present invention, the optically active amine may be produced via Reaction Scheme 3:

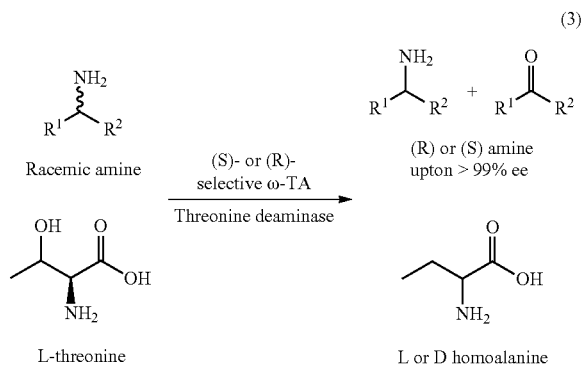

(3)

As depicted in Reaction Scheme 3, the racemic amine and the L-threonine are provided as substrates, and the threonine deaminase and the (S)- or (R)-selective ω-transaminase (ω-TA) as enzymes are provided thereto. The threonine deaminase can deaminate the L-threonine to generate 2-oxobutyrate. The 2-oxobutyrate can act as an amino acceptor and can be thus used as an expensive α-keto acid. The 2-oxobutyrate acting as an amino acceptor has considerably improved effects compared to propanal as a conventional amino acceptor.

In one embodiment of the present invention, when the (S)-selective ω-transaminase is provided in step 1), the (R)-amine and L-homoalanine can be produced from the (S)-amine of the racemic amine and the α-keto acid generated in step 2) by the action of the (S)-selective ω-transaminase in step 3). Kinetic resolution via the coupled enzyme reactions of the threonine deaminase and the (S)-selective ω-transaminase leads to production of the (R)-amine and L-homoalanine.

Alternatively, when the (R)-selective ω-transaminase is provided in step 1), the (S)-amine and D-homoalanine can be produced from the (R)-amine of the racemic amine and the α-keto acid generated in step 2) by the action of the (R)-selective ω-transaminase in step 3). Kinetic resolution via the coupled enzyme reactions of the threonine deaminase and the (R)-selective ω-transaminase leads to production of the (S)-amine and D-homoalanine.

Accordingly, when the (S)-selective ω-transaminase is provided, the (R)-amine, the ketone and the L-homoalanine may remain as final products after the reactions. Alternatively, when the (R)-selective ω-transaminase is provided, the (S)-amine, the ketone and the D-homoalanine may remain as final products after the reactions.

The threonine deaminase is not particularly limited but is preferably an enzyme derived from *Escherichia coli* and encoded by a base sequence set forth in SEQ ID NO: 7.

The (S)-selective ω-transaminase is not particularly limited so long as it can react with the α-keto acid to produce the L-amino acid. An enzyme derived from *Ochrobactrum anthropi* and encoded by a base sequence set forth in SEQ ID NO: 1 or an enzyme derived from *Paracoccus denitrifican* and encoded by a base sequence set forth in SEQ ID NO: 2 is preferably used as the (S)-selective ω-transaminase.

The (R)-selective ω-transaminase is not particularly limited so long as it can react with the α-keto acid to produce the D-amino acid. An enzyme derived from *Aspergillus terreus* and encoded by a base sequence set forth in SEQ ID NO: 3 or an enzyme derived from *Arthrobacter* sp. and encoded by a base sequence set forth in SEQ ID NO: 4 is preferably used as the (R)-selective ω-transaminase.

The racemic amine is preferably selected from the group consisting of α-methylbenzylamine, 4-fluoro-α-methylbenzylamine, α-ethylbenzylamine, 1-methyl-3-phenylpropylamine, 1-aminoindane, sec-butylamine, cyclopropylethylamine, 2-aminopentane, 2-aminooctane, 1-methoxy-2-propylamine, alaninol, and mixtures thereof.

In one preferred embodiment of the present invention, α-methylbenzylamine 1a and L-threonine 2 may be provided as substrates. In this embodiment, L-homoalanine may be produced via Reaction Scheme 4:

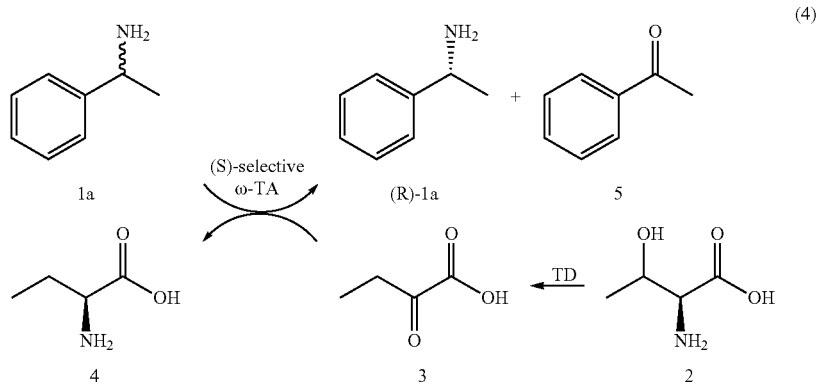

(4)

As depicted in Reaction Scheme 4, when the threonine deaminase (TD) deaminates the L-threonine 2 to generate 2-oxobutyrate 3, the (S)-selective ω-transaminase (ω-TA) selectively deaminates (S)-α-methylbenzylamine of the racemic α-methylbenzylamines 1a as a substrate and aminates the 2-oxobutyrate 3. As a result of this transamination, acetophenone 5 and L-homoalanine 4 are produced. This indicates that (R)-α-methylbenzylamine (R)-1a, L-homoalanine and acetophenone can be obtained as final products.

According to a modification of Reaction Scheme 4, an (R)-selective ω-transaminase may be used instead of the (S)-selective ω-transaminase (ω-TA). In this modification, the threonine deaminase (TD) deaminates the L-threonine to generate 2-oxobutyrate 3, the (R)-selective ω-transaminase (ω-TA) selectively deaminates the (R)-α-methylbenzylamine of the racemic α-methylbenzylamines 1a as a substrate and aminates the 2-oxobutyrate 3. As a result of this transamination, acetophenone and D-homoalanine are produced. This indicates that (S)-α-methylbenzylamine, D-homoalanine and acetophenone can be obtained as final products.

Another aspect of the present invention provides a ligand, a pharmaceutical drug or a physiologically active substance which includes an L- or R-amino acid or an L- or R-amine with high purity (≥99% ee) produced by the corresponding method. Such ligands, pharmaceutical drugs and physiologically active substances include those known in the art and those produced by all methods known in the art.

EXAMPLES

Example 1: Construction of Recombinant DNA Encoding (S)-Selective ω-Transaminase from *Ochrobactrum anthropi*

After culturing *Ochrobactrum anthropi* in an LB broth (peptone 10 g/L, yeast extract 5 g/L, sodium chloride 5 g/L, pH 7) at 37° C. for 12 h, a gene expressing an (S)-selective ω-transaminase was synthesized from a single colony of the culture. The gene was obtained by PCR amplification using DNA primers. The obtained DNA fragments were cloned into DNA pET28a(+) expression vector using NdeI and XhoI restriction enzymes and ligase. The primers used are shown in Table 1.

TABLE 1

| Primer | Base sequence |
|---|---|
| Forward primer | 5'-GATATACCATGGNNACTGCTCAG CCAAACTCT-3' (SEQ ID NO: 14) |
| Reverse primer | 5'-CGAGTGCGGCCGTCCTGGTGAGG CTTGC-3' (SEQ ID NO: 15) |

Example 2: Construction of Recombinant DNA Encoding (S)-Selective ω-Transaminase from *Paracoccus denitrificans*

After culturing *Paracoccus denitrificans* in an LB broth (peptone 10 g/L, yeast extract 5 g/L, sodium chloride 5 g/L, pH 7) at 37° C. for 12 h, a gene expressing an (S)-selective ω-transaminase was synthesized from a single colony of the culture. The gene was obtained by PCR amplification using DNA primers. The obtained DNA fragments were cloned into DNA pET28a(+) expression vector using NdeI and XhoI restriction enzymes and ligase. The primers used are shown in Table 2.

TABLE 2

| Primer | Base sequence |
|---|---|
| Forward primer | 5'-GATATACATATGAACCAACCGCA AAGC-3' (SEQ ID NO: 16) |
| Reverse primer | 5'-GTGGTGCTCGAGGGCCACCTCGG CAAA-3' (SEQ ID NO: 17) |

Example 3: Construction of Recombinant DNA Consisting of DNA Encoding (R)-Selective ω-Transaminase from *Aspergillus terreus* and Vector DNA After an (R)-selective ω-transaminase gene sequence (NCBI gene ID: 115385557) derived from *Aspergillus terreus* was synthesized in pGEM-T vector, a gene expressing the (R)-selective ω-transaminase was synthesized from a plasmid. The gene was obtained by PCR amplification using DNA primers. The obtained DNA fragments were cloned into DNA pET28a(+) expression vector using NcoI and XhoI restriction enzymes. The primers used are shown in Table 3.

TABLE 3

| Primer | Base sequence |
|---|---|
| Forward primer | 5'-AGAAGGAGATATACCATGGCCTC CATGGACAAAGTCT-3' (SEQ ID NO: 18) |
| Reverse primer | 5'-GGTGGTGGTGGTGCTCGAGGTTC CTCTCGTTATAATC-3' (SEQ ID NO: 19) |

Example 4: Construction of Recombinant DNA Encoding D-Amino Acid Transaminase Derived from *Bacillus sphaericus*

After a D-amino acid transaminase gene sequence (NCBI gene ID: 849138) derived from *Bacillus sphaericus* was synthesized in pGEM-T vector, a gene expressing the D-amino acid transaminase was synthesized from a plasmid. The gene was obtained by PCR amplification using synthetic DNA primers. The obtained DNA fragments were cloned into DNA pET28a(+) expression vector using Nco1 and Xho1 restriction enzymes. The primers used are shown in Table 4.

TABLE 4

| Primer | Base sequence |
|---|---|
| Forward primer | 5'-GATATACCATGGCATACTCATTA TGG-3' (SEQ ID NO: 20) |
| Reverse primer | 5'-GTGGTGCTCGAGGGCATTAATTG AAATTGG-3' (SEQ ID NO: 21) |

Example 5: Construction of Recombinant DNA Encoding L-Amino Acid Transaminase Derived from *Escherichia coli*

After a branched-chain L-amino acid transaminase gene sequence derived from *Escherichia coli* was synthesized in pGEM-T vector, a gene expressing the branched-chain L-amino acid transaminase was obtained from a plasmid by PCR amplification using synthetic DNA primers. The obtained DNA fragments were cloned into DNA pET28a(+) expression vector using Nco1 and Xho1 restriction enzymes.

Example 6: Construction of Recombinant DNA Consisting of DNA Encoding Threonine Deaminase from *Escherichia coli* and Vector DNA After culturing *Escherichia coli* in an LB broth (peptone 10 g/L, yeast extract 5 g/L, sodium chloride 5 g/L, pH 7) at 37° C. for 12 h, a gene expressing a threonine deaminase was synthesized from a single colony of the culture. The gene was obtained by PCR amplification using DNA primers. The obtained DNA fragments were cloned into DNA pET28a(+) expression vector using Nde1 and Xho1 restriction enzymes and ligase. The primers used are shown in Table 5.

TABLE 5

| Primer | Base sequence |
|---|---|
| Forward primer | 5'-GATATACATATGGCTGACTCGCA ACCCCTG-3' (SEQ ID NO: 22) |
| Reverse primer | 5'-GTGGTGCTCGAGACCCGCCAAAA AGAA-3' (SEQ ID NO: 23) |

Example 7: Overexpression and Purification of Enzymes from Transformed Strain

*E. coli* BL21 (DE3) was transformed with each of the plasmids obtained in Examples 1-6. After culturing DE3 in 300 mL of an LB broth containing kanamycin, IPTG (final concentration 1 mM) at an optical density (OD) of 0.5 was added thereto. Thereafter, the mixture was incubated at 37° C. for 6 h or more and centrifuged at 10000×g and at 4° C. for 20 min. The bacterial cells were suspended in 15 mL of resuspension buffer (50 Mm Tris-HCl, 50 mM calcium chloride, 1 mM β-mercaptoethanol, 0.1 mM PMSF, 20 μM PLP, pH 7). The suspension was sonicated under ice cooling and centrifuged at 17000×g and 4° C. for 30 min. Purification of the supernatant as a crude extract by affinity chromatography afforded a solution of the desired enzyme, i.e. (S)-selective ω-transaminase, (R)-selective ω-transaminase, D-amino acid transaminase, L-amino acid transaminase, or threonine deaminase.

Example 8: Activity and Concentration Determination of the Purified Enzymes

The activity and concentration of each enzyme were determined in 50 mM potassium phosphate at 37° C. and pH 7. 10 min after initiation of the enzyme reaction for activity measurement, 600 μl of acetonitrile was added to 100 μl of the reaction solution to stop the reaction.

One unit of the activity of each (S)- or (R)-selective ω-transaminase purified in Examples 1-3 is defined as the enzyme amount catalyzing the formation of 1 μmole of acetophenone in 1 min at 20 mM pyruvate and 20 mM (S)-α-methylbenzylamine. One unit of the activity of each D- or L-selective transaminase purified in Examples 4-5 is defined as the enzyme amount catalyzing the formation of 1 μmole of pyruvate in 1 min at 20 mM D-alanine and 2-oxobutyrate. One unit of the activity of the threonine deaminase purified in Example 7 is defined as the enzyme amount catalyzing the formation of 1 μmole of 2-oxobutyrate in 1 min at 0.1 mM PLP and 50 mM L-threonine.

The activities of the (S)- or (R)-selective ω-transaminase, the D- or L-amino acid transaminase, and the threonine deaminase were determined by measuring the amounts of acetophenone, pyruvate, and 2-oxobutyrate using HPLC, respectively.

Example 9: Analysis of the Amines and Amino Acids

In this example, the concentrations of the products were analyzed and the enantiomeric excess (ee) values of the products were calculated. To this end, each of the chiral amines and amino acids was derivatized with GITC and Marfey reagents and analyzed by high-performance liquid chromatography (HPLC). The GITC derivatization was performed by the following general procedure. First, a reaction sample of each amine or amino acid (≤0.5 mM) was mixed with a solution of 1.5 mM GITC and 1.5 mM triethylamine in acetonitrile as a derivatization solution in a ratio of 1:1, and the reaction was allowed to proceed at room temperature for at least 35 min. Then, analysis was conducted using C18 column and HPLC under the following conditions: flow rate=1 ml/min, detection=UV at 254 nm. The Marfey reagent derivatization was performed by the following procedure. First, 10 μl of each sample was mixed with 8 μl of 1 M sodium bicarbonate and 40 μl of 1% Marfey reagent. The mixture was allowed to react at 40° C. for 1 h. The reaction mixture was cooled and mixed with 8 μl of 1 M hydrochloric acid. The resulting solution was mixed with 434 μl of a 40% acetonitrile solution. Then, analysis was conducted using C18 column and HPLC under the following conditions: flow rate=1 ml/min, temperature=40° C., detection=UV at 320 nm. The results are shown in Table 6. The enantiomeric excess values were calculated from the concentrations of the (S)-enantiomers ($C_s$) and (R)-enantiomers ($C_R$) measured above by the following equation:

$$\% \ ee^R = \frac{(C_R - C_S)}{(C_R + C_S)} \times 100$$

In Table 6, 1a, 1b, 1c, 1d, 1e, 1f, 1g, 1h, 1i, 1j, and 1k represent α-methylbenzylamine, 4-fluoro-α-methylbenzylamine, α-ethylbenzylamine, 1-methyl-3-phenylpropylamine, 1-aminoindane, sec-butylamine, cyclopropylethylamine, 2-aminopentane, 2-aminooctane, 1-methoxy-2-propylamine, and alaninol, respectively.

TABLE 6

| | | Reaction time (min) | |
|---|---|---|---|
| | Elution condition[a] | (R)-form | (S)-form |
| GITC derivatization | | | |
| 1a | Isocratic elution with A55%, B45% | 14.5 | 16.2 |
| 1b | Isocratic elution with A55%, B45% | 18.7 | 21.5 |
| 1c | Isocratic elution with A55%, B45% | 24.5 | 26.4 |
| 1d | Isocratic elution with A55%, B45% | 39.4 | 42.0 |
| 1e | Gradient elution from A60%, B40% to A50% | 14.1 | 16.6 |
| 1f | Isocratic elution with A50%, B50% | 13.3 | 14.4 |
| 1h | Isocratic elution with A50%, B50% | 27.5 | 30.6 |
| 1i | Isocratic elution with A65%, B35% | 23.6 | 25.4 |
| 1j | Gradient elution from A60%, B40% from A65%, B35% | 24.9 | 27.0 |
| 4 | Isocratic elution with A55%, B45% | 5.3 | 4. |
| Alanine | Isocratic elution with A50%, B50% | 5.6 | 4.6 |
| Marfey reagent derivatization | | | |
| 1g | Isocratic elution with A50%, B50% | 26.9 | 28.5 |
| 1k | Isocratic elution with A55%, B45% | 4.9 | 3.3 |

Note -
A: methanol (0.1% TFA),
B: TDW (0.1% TFA)

Example 10: Substrate Specificities of the Purified D-Amino Acid Transaminase Toward Keto Acids and Conversion of Optically Active Amino Acids by Keto Acids Each of amino acceptors shown in Tables 7 and 8 and D-alanine or D-homoalanine as substrates were allowed to react with the D-amino acid transaminase purified in Example 7. Specifically, each amino acceptor (20 mM), D-alanine or D-homoalanine (20 mM), and potassium phosphate (50 mM, pH 7) were allowed to react with 0.1 U/ml of the D-amino acid transaminase at 37° C. for 10 min, and the amount of a keto acid (pyruvate or 2-oxobutyrate) generated was measured. The D-amino acid transaminase was shown to have activity toward the amino acceptors, including 2-oxobutyrate, β-hydroxypyruvate, mercaptopyruvate, fluoropyruvate, 3-methyl-2-oxobutyrate, 2-oxopentanoate, 4-methyl-2-oxopentanoate, 2-ketohexanoate, α-ketoglutarate, phenylpyruvate, and pyruvate. The results are shown in Tables 7 and 8.

TABLE 7

| Substrates | | Products | |
|---|---|---|---|
| Amino acceptor | Amino donor | D-amino acid | Pyruvate (mM) |
| 2-Oxobutyrate | D-Alanine | Homoalanine | 1.375 |
| β-Hydroxypyruvate | D-Alanine | Serine | 0.079 |
| Mercaptopyruvate | D-Alanine | Cysteine | 0.022 |
| Fluoropyruvate | D-Alanine | Fluoroalanine | 0.053 |
| Bromopyruvate | D-Alanine | Bromoalanine | 0.000 |
| 3-Methyl-2-oxobutyrate | D-Alanine | Valine | 0.014 |
| Trimethylpyruvate | D-Alanine | tert-leucine | 0.000 |
| 2-Oxopentanoate | D-Alanine | Norvaline | 0.882 |
| 4-Methyl-2-oxopentanoate | D-Alanine | Leucine | 0.073 |
| 2-Ketohexanoate | D-Alanine | Norleucine | 0.531 |
| α-Ketoglutarate | D-Alanine | Glutamate | 0.971 |
| Phenyl glyoxylate | D-Alanine | Phenylglycine | 0.000 |
| Phenylpyruvate | D-Alanine | Phenylalanine | 0.075 |
| 2-(3-Hydroxy-1-adamantyl)-oxoethanoate | D-Alanine | 3-hydroxy-adamantylglycine | 0.000 |

TABLE 8

| Substrates | | Products | |
|---|---|---|---|
| Amino acceptor | Amino donor (D-amino acid) | D-amino acid | 2-Oxobutyrate (mM) |
| Pyruvate | D-Homoalanine | Alanine | 0.399 |
| 2-Oxopentanoate | D-Homoalanine | Norvaline | 0.651 |

Example 11: Confirmation Whether L-Amino Acid Concentration Deteriorates the Activity of the Purified D-Amino Acid Transaminase For continuous deracemization of a racemic amino acid with the D-amino acid transaminase purified in Example 7, L-amino acid as a final product should not affect the activity of the D-amino acid transaminase. Deterioration in the activity of the enzyme by the final product makes it difficult to induce continuous reactions. The activities of the D-amino acid transaminase were confirmed at different concentrations (0, 1, 3, 5, 7, 10, 15, and 20 mM) of L-homoalanine in 20 mM D-homoalanine, 20 mM pyruvate, and 50 mM potassium phosphate (pH 7). After the reactions were carried out at 37° C. for 10 min, the amounts of 2-oxobutyrate produced were measured. The results are shown in FIG. 1. FIG. 1 shows that the D-amino acid transaminase did not lose its activity by the final product L-amino acid.

Example 12: Substrate Specificities of the Purified ω-Transaminases Toward Keto Acids and Conversion of Optically Active Amino Acids by Keto Acids An investigation was made as to the substrate specificities of each of the (S)-selective ω-transaminases derived from *O. anthropi* and *P. denitrificans*, which were purified in Example 7, toward keto acids. The substrate specificity of the (S)-selective ω-transaminase was confirmed in each keto acid (20 mM), (S)-α-methylbenzylamine (20 mM) and potassium phosphate (50 mM, pH 7). After the reactions were carried out at 37° C. for 10 min, the amounts of acetophenone produced were measured. The (S)-selective ω-transaminase was shown to have activity toward glyoxylate, pyruvate, 2-oxobutyrate, β-hydroxypyruvate, fluoropyruvate, 2-oxopentanoate, 4-methyl-2oxopentanoate (*P. denitrificans*), and 2-ketohexanoate. The results are shown in Table 9.

*anthropi* and *P. denitrificans*, which were purified in Example 7, toward amines. The substrate specificity of the (S)-selective ω-transaminase was confirmed in each amine (20 mM), (S)-amine (20 mM, in 40 mM racemic sec-butylamine) and potassium phosphate (50 mM, pH 7). After the reactions were carried out at 37° C. for 10 min, the amounts of L-alanine produced were measured. The (S)-selective ω-transaminase was shown to have activity toward

TABLE 9

| Substrates | | Products | | |
|---|---|---|---|---|
| Amino acceptor | Amino donor | | Acetophenone (mM) | |
| (keto acid) | ((S)-amine) | L-amino acid | O. anthropi | P. denitrificans |
| Glyoxylate | (S)-α-methylbenzylamine | Glycine | 1.733 | 1.076 |
| Pyruvate | (S)-α-methylbenzylamine | Alanine | 1.284 | 1.216 |
| 2-Oxobutyrate | (S)-α-methylbenzylamine | Homoalanine | 0.173 | 0.821 |
| β-Hydroxypyruvate | (S)-α-methylbenzylamine | Serine | 0.183 | 0.066 |
| Mercaptopyruvate | (S)-α-methylbenzylamine | Cysteine | 0.012 | 0.008 |
| Fluoropyruvate | (S)-α-methylbenzylamine | Fluoroalanine | 0.554 | 0.339 |
| Bromopyruvate | (S)-α-methylbenzylamine | Bromoalanine | 0.010 | −0.001 |
| 3-Methyl-2-oxobutyrate | (S)-α-methylbenzylamine | Valine | −0.001 | −0.002 |
| Trimethylpyruvate | (S)-α-methylbenzylamine | tert-leucine | −0.002 | −0.004 |
| 2-Oxopentanoate | (S)-α-methylbenzylamine | Norvaline | 0.078 | 1.032 |
| 4-Methyl-2-oxopentanoate | (S)-α-methylbenzylamine | Leucine | 0.005 | 0.175 |
| 3-Methyl-2-oxopentanoate | (S)-α-methylbenzylamine | Isoleucine | 0.001 | −0.004 |
| 2-Ketohexanoate | (S)-α-methylbenzylamine | Norleucine | 0.006 | 0.713 |
| α-Ketoglutarate | (S)-α-methylbenzylamine | Glutamate | −0.001 | −0.003 |
| Phenylglyoxylate | (S)-α-methylbenzylamine | Phenylglycine | −0.005 | −0.008 |
| 2-(3-hydroxy-1-adamantyl)-oxoethanoate | (S)-α-methylbenzylamine | 3-hydroxyadamantyl glycine | −0.002 | −0.004 |

The results in Table 9 show that α-ketoglutarate had no activity toward the ω-transaminase. In contrast, the results in Tables 7 and 8 show that α-ketoglutarate had activity toward the D-amino acid transaminase. In conclusion, α-ketoglutarate can be considered as an example of preferred amino acceptors.

Example 13: Substrate Specificities of the Purified ω-Transaminases Toward Amines and Conversion of L-Alanine from Pyruvate An investigation was made as to the substrate specificities of each of the (S)-selective ω-transaminases derived from *O.*

(S)-α-methylbenzylamine, isopropylamine, and sec-butylamine. The results are shown in Table 10.

TABLE 10

| Substrates | | | Products | |
|---|---|---|---|---|
| Amino donor | Amino acceptor | | L-alanine (mM) | |
| (Amine) | (Keto acid) | Ketone | O. anthropi | P. denitrificans |
| (S)-α-methylbenzylamine | Pyruvate | Acetophenone | 0.715 ± 0.082 | 0.451 ± 0.077 |
| sec-butylamine | Pyruvate | 2-Butanone | 0.164 ± 0.019 | 0.000 ± 0.000 |
| Isopropylamine | Pyruvate | Acetone | 0.309 ± 0.050 | 0.033 ± 0.002 |

EXPERIMENTAL EXAMPLES

Figure 2:
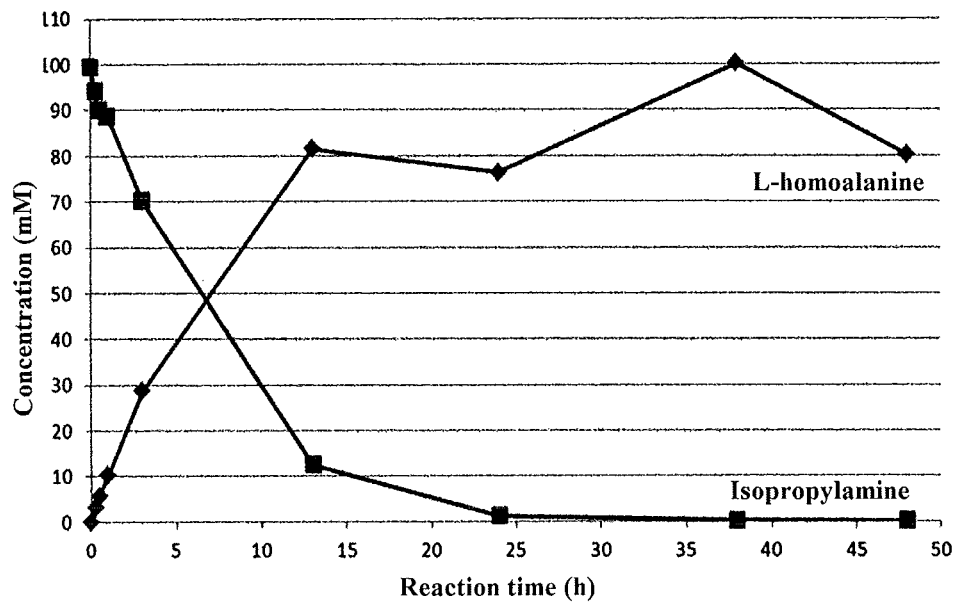
FIG. 2 is a graph showing the conversion to an L-amino acid when isopropylamine was used as an amino donor.

Experimental Example 1: Production of High Concentration of L-Amino Acid from Keto Acid by Using the Purified ω-Transaminase and Isopropylamine as Amino Donor An experiment was carried out to confirm whether the use of the ω-transaminase purified in Example 7 led to the production of a high concentration of an L-amino acid from a keto acid. Specifically, after 1 U/ml ω-transaminase was allowed to react in 100 mM 2-oxobutyrate as a keto acid, 100 mM isopropylamine as an amino donor, and 50 mM potassium phosphate (pH 7) at 37° C., the amounts of L-homoalanine produced were measured as a function of time. The reaction of the purified ω-transaminase and the use of the amino donor were confirmed to lead to the production of a high concentration of L-homoalanine from the keto acid with ≥80% conversion. The results are shown in FIG. 2.

Figure 3:
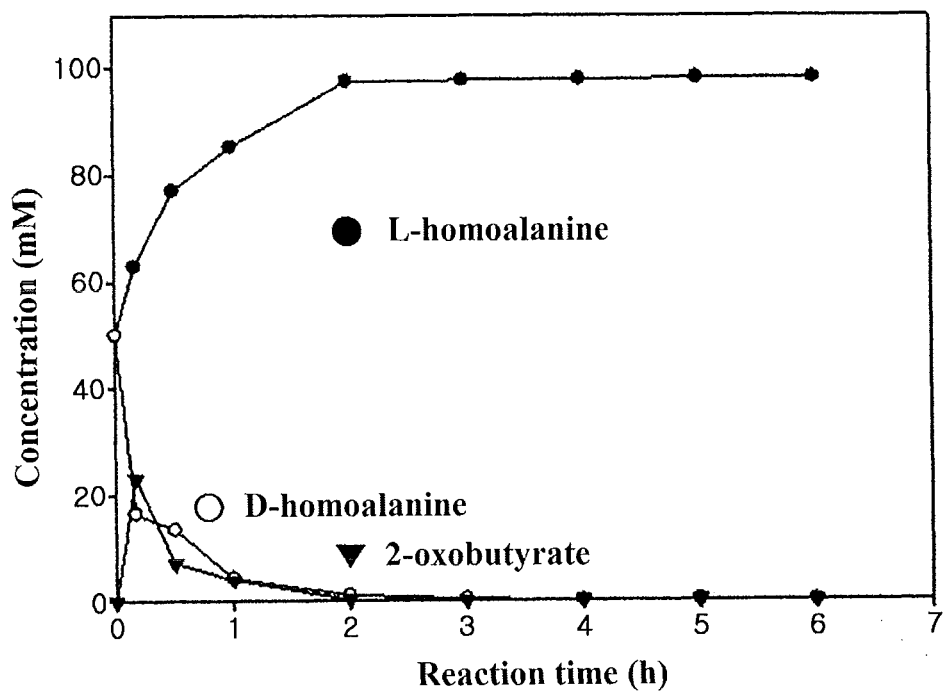
FIG. 3 is a graph showing the throughput of L-homoalanine from racemic homoalanine according to one embodiment of the present invention.
Figure 4:
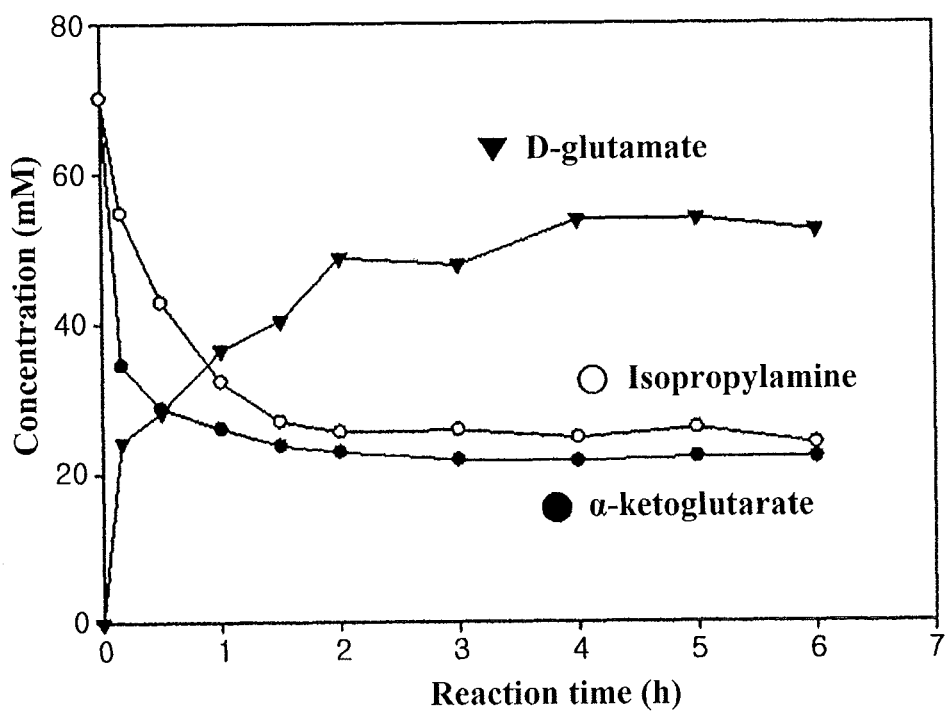
FIG. 4 is a graph showing changes in the concentration of α-ketoglutarate and isopropylamine as substrates and D-glutamate as a final product as a function of reaction time according to one embodiment of the present invention.

Experimental Example 2: Conversion of High Concentrations of Racemic Amino Acids to L-Amino Acids by Coupling Reactions of the Purified D-Amino Acid Transaminase and (S)-Selective ω-Transaminase An experiment was carried out to confirm whether the use of the D-amino acid transaminase and (S)-selective ω-transaminase purified in Example 7 led to the production of L-amino acids from high concentrations of racemic amino acids. Specifically, coupling reactions of the D-amino acid transaminase (4 U/ml) and the (S)-selective ω-transaminase (20 U/ml) were allowed to proceed in each racemic amino acid (100 mM), α-ketoglutarate, phenylglyoxylate or phenylpyruvate (70 mM) as an amino acceptor, isopropylamine (70 mM) as an amino donor, PLP (0.1 mM), and potassium phosphate (50 mM, pH 7). In the case of leucine and norleucine, each racemic amino acid (50 mM), α-ketoglutarate, phenyl glyoxylate or phenylpyruvate (35 mM), and isopropylamine (35 mM) as substrates were used for the reaction. In the case of deracemization for alanine production, the amounts of the substrates and products were measured as a function of reaction time. In the case of homoalanine, serine, homoserine, norvaline, leucine, and norleucine, their D-amino acids and L-amino acids were analyzed. L-amino acids with ≥99% enantiomeric excess (ee) were produced from 100 mM racemic amino acids (each 50 mM for leucine and norleucine) via deracemization. The results are shown in FIG. 3, FIG. 4 and Table 11.

TABLE 11

| Amino acid | Final concentration of L-amino acid (mM) | ee (%) | Reaction time (h) |
|---|---|---|---|
| Alanine | 100.15 | 99.34 | 10 |
| Homoalanine | 99.24 | 99.94 | 6 |
| Serine | 101.84 | 98.92 | 25 |
| Norvaline | 103.86 | 99.16 | 25 |
| Norleucine | 55.29 | 99.30 | 20 |
| Leucine | 49.66 | 99.81 | 10 |
| Homoserine | 98.51 | 98.87 | 25 |

Experimental Example 3: Conversion of High Concentrations of Racemic Amino Acids to D-Amino Acids by Coupling Reactions of the Purified Branched-Chain L-Amino Acid Transaminase and (R)-Selective ω-Transaminase An experiment was carried out to confirm whether the use of the branched-chain L-amino acid transaminase and (R)-selective ω-transaminase purified in Example 7 led to the production of D-amino acids from high concentrations of racemic amino acids. Specifically, coupling reactions of the branched-chain L-amino acid transaminase (4 U/ml) and the (S)-selective ω-transaminase (20 U/ml) were allowed to proceed in each racemic amino acid (100 mM), α-ketoglutarate (70 mM), isopropylamine (70 mM), PLP (0.1 mM), and potassium phosphate (50 mM, pH 7). In the case of norleucine, the racemic amino acid (50 mM), α-ketoglutarate (35 mM), and isopropylamine (35 mM) as substrates were used for the reaction. In the case of alanine, homoalanine, serine, homoserine, norvaline, leucine, and norleucine, their D-amino acids and L-amino acids were analyzed. L-amino acids with ≥99% enantiomeric excess (ee) were produced from 100 mM racemic amino acids (50 mM for norleucine) via deracemization. The results are shown in Table 12.

TABLE 12

| Amino acid | Final concentration of L-amino acid (mM) | ee (%) | Reaction time (h) |
|---|---|---|---|
| Alanine | 102.88 | 99.10 | 20 |
| Homoalanine | 99.54 | 99.82 | 15 |
| Serine | 100.71 | 99.01 | 20 |
| Norvaline | 98.42 | 99.01 | 20 |
| Norleucine | 48.58 | 99.51 | 20 |
| Homoserine | 97.78 | 98.89 | 25 |

Figure 5:
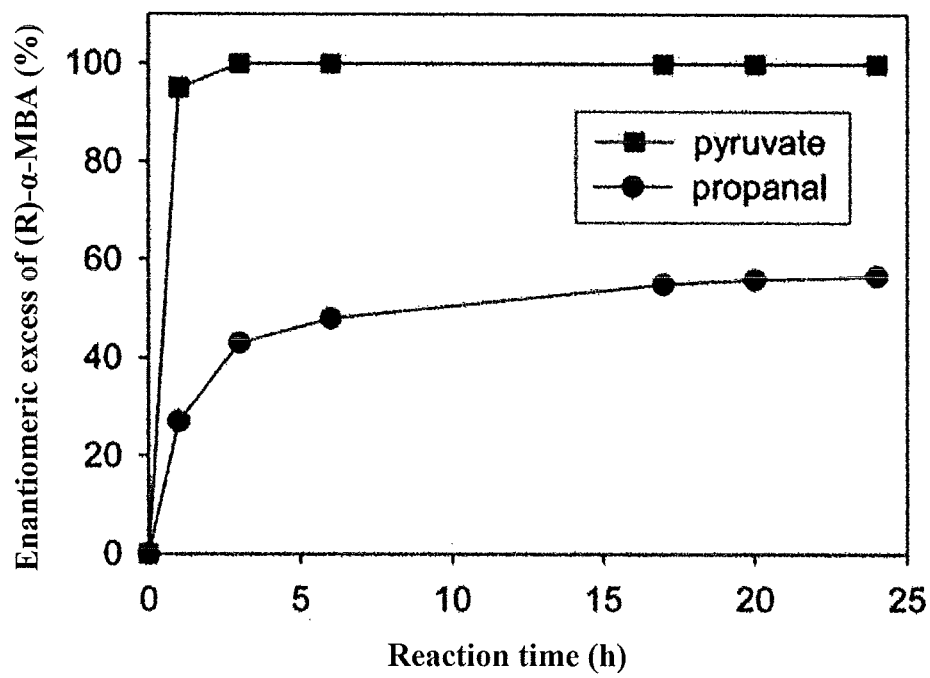
FIG. 5 is a graph comparing the activities of pyruvate and propanal as amino acceptors for an ω-transaminase.

Experimental Example 4: Comparison of Activities of Pyruvate and Propanal as Amino Acceptors for Kinetic Resolution of Optically Active Chiral Amines Using the Purified ω-Transaminase Racemic α-methylbenzylamine and pyruvate or propanal as substrates were allowed to react using the (S)-selective ω-transaminase purified in Example 7. After 5 U/ml of the (S)-selective ω-transaminase derived from O. anthropi was added to 100 mM α-methylbenzylamine, 80 mM pyruvate or propanal, 0.1 mM PLP, and 50 mM phosphate buffer (pH 7.5) at 37° C., the amounts of the (S)-α-methylbenzylamine and (R)-α-methylbenzylamine produced were measured with time and the enantiomeric excess values thereof were calculated. The enatiomeric excess (ee) of the (R)-α-methylbenzylamine reached ≥99% with pyruvate at 3 h, whereas that of the (R)-α-methylbenzylamine was only 57% with propanal even after the reaction for 24 h. The results are shown in FIG. 5.

Experimental Example 5: Investigation of Substrate Specificities of the Purified ω-Transaminase Toward Amines An investigation was made as to the substrate specificities of the (S)-selective ω-transaminase derived from O. anthropi, which was purified in Example 7, toward 11 amines: α-methylbenzylamine 1a, 4-fluoro-α-methylbenzylamine 1b, α-ethylbenzylamine 1c, 1-methyl-3-phenylpropylamine 1d, 1-aminoindane 1e, sec-butylamine 1f, cyclopropylethylamine 1g, 2-aminopentane 1h, 2-aminoooctane 1i, 1-methoxy-2-propylamine 1j, and alaninol 1k. 0.125 U/ml of the (S)-selective transaminase derived from O. anthropi was added to each racemic amine (10 mM), pyruvate (10 mM), PLP (0.1 mM), and phosphate buffer (50 mM, pH 7.5) at 37° C. After the mixture was allowed to react for 10 min, the amount of L-alanine produced was measured via GITC derivatization. All activities were measured in the initial reaction rate range of ≤5% conversion. The initial reaction rate for α-methylbenzylamine was measured to be 0.033 mM/min. When the activity of the ω-transaminase toward α-methylbenzylamine was defined as 100%, the activities of the ω-transaminase toward 4-fluoro-α-methylbenzylamine 1b, α-ethylbenzylamine 1c, 1-methyl-3-phenylpropylamine 1d, and 1-aminoindane 1e as arylalkylamines were 91%, 18%, 70%, and 64%, respectively. The activity of the ω-transaminase toward (S)-1-aminoindane was 153% of that toward (S)-α-methylbenzylamine. The activities of the ω-transaminase toward sec-butylamine 1f, cyclopropylethylamine 1g, 2-aminopentane 1h, 2-aminooctane 1i, 1-methoxy-2-propylamine 1j, and alaninol 1k as alkylamines were 54%, 63%, 29%, 146%, 60%, and 63%, respectively. The results are shown in Table 13.

TABLE 13

| Substrate | R¹ | R² | Relative reactivity (%) |
|---|---|---|---|
| 1a | C$_6$H$_5$ | CH$_3$ | 100$^c$ |
| 1b | p-F—C$_6$H$_4$ | CH$_3$ | 91 |
| 1c | C$_6$H$_5$ | CH$_2$CH$_3$ | 18 |
| 1d | C$_6$H$_5$(CH$_2$)$_2$ | CH$_3$ | 70 |
| 1e | (indane-NH$_2$) | | 64 (153)$^d$ |
| 1f | CH$_3$CH$_2$ | CH$_3$ | 54 |
| 1g | Cyclopropyl | CH$_3$ | 63 |
| 1h | CH$_3$(CH$_2$)$_2$ | CH$_3$ | 29 |
| 1i | CH$_3$(CH$_2$)$_5$ | CH$_3$ | 146 |
| 1j | CH$_3$OCH$_2$ | CH$_2$ | 60 |
| 1k | HOCH$_2$ | CH$_3$ | 63 |

Experimental Example 6: Yields of Optically Active Chiral Amines According to Changes in the Concentration of Threonine Deaminase and ω-Transaminase when Kinetic Resolution was Performed Via Coupled Enzyme Reactions of the Enzymes Coupled enzyme reactions of the threonine deaminase and ω-transaminase purified in Example 7 were carried out at varying enzyme concentrations shown in Table 14. The reaction conditions were as follows: 100 mM racemic methylbenzylamine, 60 mM L-threonine, 0.1 mM PLP, and 50 mM phosphate buffer (pH 7.5) at 37° C. for 2.5 h. Increasing ω-transaminase concentrations (1.25 U/ml, 2.50 U/ml, and 3.75 U/ml) at a constant threonine deaminase (9 U/ml) led to an increase in the enantiomeric excess of (R)-α-methylbenzylamine (28%, 65%, and 90%). In contrast, increasing threonine deaminase concentrations (9 U/ml, 18 U/ml, and 27 U/ml) at a constant ω-transaminase concentration (1.25 U/ml) did not lead to an improvement in the enantiomeric excess of (R)-α-methylbenzylamine (28%, 24%, and 26%). This result indicates that the ω-transaminase reaction is a rate-determining step of the coupled enzyme reactions. Therefore, a higher ω-transaminase concentration is preferred for a higher enantiomeric excess of (R)-α-methylbenzylamine. The results are shown in Table 14.

TABLE 14

| ω-TA (U mL⁻¹) | TD (U mL⁻¹) | 4$^a$ (mM) | ee (%) of (R)-1a$^b$ |
|---|---|---|---|
| 1.25 | 9 | 15 | 28 |
| 2.50 | 9 | 33 | 65 |
| 3.75 | 9 | 47 | 90 |
| 1.25 | 18 | 19 | 24 |
| 1.25 | 27 | 13 | 26 |

Note:
ω-TA: ω-transaminase,
TD: threonine deaminase,
$^a$concentration determined by a standard calibration method from HPLC analysis of the GITC derivative,
$^b$determined by HPLC analysis of the GITC derivatives Experimental Example 7: Yields of (R)-Amines and Production of L-Homoalanine Via Coupled Enzyme Reactions of (S)-Selective ω-Transaminase and Threonine Deaminase Using L-Threonine and Racemic Amines as Substrates Referring to the enzyme proportions yielding the best outcome in Experimental Example 6, kinetic resolution of 11 amines was performed and L-homoalanine was produced via coupled enzyme reactions of the ω-transaminase and threonine deaminase purified in Example 7. The amines were α-methylbenzylamine 1a, 4-fluoro-α-methylbenzylamine 1b, α-ethylbenzylamine 1c, 1-methyl-3-phenylpropylamine 1d, 1-aminoindane 1e, sec-butylamine 1f, cyclopropylethylamine 1g, 2-aminopentane 1h, 2-aminooctane 1i, 1-methoxy-2-propylamine 1j, and alaninol 1k. After addition of the (S)-selective ω-transaminase (3.75 U/ml) and the threonine deaminase (9 U/ml) to each of the amines 1a-1k (100 mM), L-threonine (60 mM), PLP (0.1 mM), and phosphate buffer (50 mM, pH 7.5), the concentration and enantiomeric excess of each amine were measured. All the amines except α-ethylbenzylamine 1c, 2-aminooctane 1i, and alaninol 1k had enantiomeric excess values ≥99% within a reaction time of 10 h. For kinetic resolution of α-ethylbenzylamine 1c, 2-aminooctane 1i, and alaninol 1k, the ω-transaminase concentration, which is a rate determining step of the coupled enzyme reactions, was increased to 10 U/ml. As a result, enantiomeric excess values of α-ethylbenzylamine 1c and 2-aminooctane 1i higher than 99% were attained, and an enantiomeric excess of 66% was attained for alaninol 1k within 30 h. In all reactions, the production of L-homoalanine with 99% enantiomeric excess was confirmed. The results are shown in Table 15.

TABLE 15

| Chiral amine | Reaction time (h) | Conversion (%) | ee of (R)-amine (%) |
|---|---|---|---|
| 1a | 3 | 49.9 | >99 |
| 1b | 3.5 | 50.5 | >99 |
| 1c | 28 | 35.1 | 52 |
| 1c | 30 | 50.1 | >99 |
| 1d | 5 | 50.9 | >99 |
| 1e | 7 | 50.0 | >99 |
| 1f | 8 | 50.2 | >99 |
| 1g | 8 | 50.1 | >99 |
| 1h | 9 | 50.5 | >99 |
| 1i | 24 | 37.4 | 58 |
| 1i | 24 | 50.2 | >99 |
| 1j | 9 | 50.6 | >99 |
| 1k | 30 | 40.8 | 66 |

Figure 6:
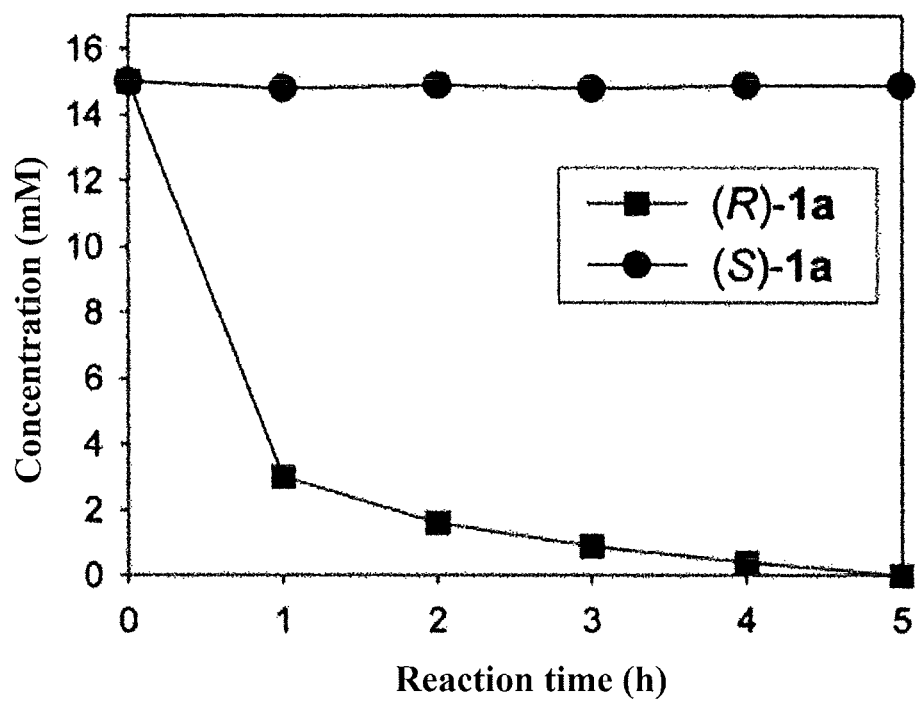
FIG. 6 is a graph showing changes in the concentration of (S)-α-methylbenzylamine and (R)-α-methylbenzylamine as a function of reaction time when an (R)-selective ω-transaminase was used in accordance with the present invention.

Experimental Example 8: Yields of (S)-Amines and Production of D-Homoalanine Via Coupled Enzyme Reactions of (R)-Selective ω-Transaminase and Threonine Deaminase Using L-Threonine and Racemic Amines as Substrates Kinetic resolution of amines was performed and D-homoalanine was produced via coupled enzyme reactions of the (R)-selective ω-transaminase and threonine deaminase purified in Example 7. After addition of the (R)-selective ω-transaminase (1.5 U/ml) and the threonine deaminase (4.5 U/ml) to α-methylbenzylamine (30 mM), L-threonine (20 mM), PLP (0.1 mM), and phosphate buffer (50 mM, pH 7.5), the concentrations of (S)-α-methylbenzylamine and (R)-α-methylbenzylamine were measured as a function of reaction time. An enantiomeric excess ≥99% was obtained within a reaction time of 5 h. Likewise, D-homoalanine was produced with ≥99% enantiomeric excess. The results are shown in FIG. 6.

According to the methods of the present invention, α-keto acids are generated as reaction intermediates, eliminating the need to use expensive α-keto acids as starting materials. In addition, optically active amine compounds produced by the methods of the present invention can be widely used in various industrial applications, including pharmaceutical and agrochemical industries that require chiral compounds, due to their high enantiomeric excess (≥99%).

---

We claim:

1. A one-pot method for producing an optically pure amino acid by deracemizing a racemic amino acid with two transaminases of opposite enantioselectivity and a co-substrate dedicated for each transaminase, comprising:
   1) providing a racemic amino acid, an amino acceptor for an amino acid transaminase, and an amino donor for a co-transaminase, to the amino acid transaminase and the ω-transaminase whose enantioselectivities are opposite to each other;
   2) contacting the racemic amino acid, the amino acceptor, and the amino acid transaminase provided in step 1) to convert one amino acid enantiomer of the racemic amino acid to an α-keto acid; and
   3) contacting the α-keto acid produced in step 2), the amino donor provided in step 1), and the ω-transaminase provided in step 1) to convert the α-keto acid to the amino acid enantiomer whose chirality is opposite to the amino acid enantiomer reacted in step 2),
   wherein an (R)-amino acid transaminase and a (S)-selective ω-transaminase are used as the amino acid transaminase and the ω-transaminase, respectively, to deracemize the racemic amino acid into optically pure (S)-amino acid, or
   wherein a (S)-amino acid transaminase and an (R)-selective ω-transaminase are used as the amino acid transaminase and the ω-transaminase, respectively, to deracemize the racemic amino acid into optically pure (R)-amino acid.

2. The one-pot method according to claim 1, wherein the (R)-amino acid transaminase is provided in step 1), the (R)-amino acid of the racemic amino acid and the amino acceptor are contacted with the R-amino acid transaminase to produce an α-keto acid in step 2), and the α-keto acid is contacted with the (S)-selective ω-transaminase to produce a (S)-amino acid of the α-keto acid in step 3).

3. The one-pot method according to claim 1, wherein the (S)-amino acid transaminase is provided in step 1), the (S)-amino acid of the racemic amino acid and the amino acceptor are contacted with the (S)-amino acid transaminase to produce an α-keto acid in step 2), and the a-keto acid is contacted with the (R)-selective ω-transaminase to produce an (R)-amino acid of the a-keto acid in step 3).

4. The one-pot method according to claim 1, wherein the (S)-selective ω-transaminase is an enzyme derived from *Ochrobactrum anthropi* and encoded by the nucleic acid sequence set forth in SEQ ID NO: 1 or an enzyme derived from *Paracoccus denitrificans* and encoded by the nucleic acid sequence set forth in SEQ ID NO: 2.

5. The one-pot method according to claim 1, wherein the (R)-selective co-transaminase is an enzyme derived from *Aspergillus terreus* and encoded by the nucleic acid sequence set forth in SEQ ID NO: 3 or an enzyme derived from *Arthrobacter* sp. and encoded by the nucleic acid sequence set forth in SEQ ID NO: 4.

6. The one-pot method according to claim 1, wherein the racemic amino acid is selected from the group consisting of racemic alanine, racemic serine, racemic homoserine, racemic norvaline, racemic norleucine, racemic leucine, and mixtures thereof.

7. The one-pot method according to claim 1, wherein the amino acceptor is selected from the group consisting of a-ketoglutarate, phenylglyoxylate, phenylpyruvate, and mixtures thereof.

8. The one-pot method according to claim 1, wherein the amino donor is selected from the group consisting of isopropylamine, methylbenzylamine, benzylamine, and mixtures thereof.

9. The one-pot method according to claim 1, wherein the (R)-selective amino acid transaminase is an enzyme derived from *Bacillus sphaericus* and encoded by the nucleic acid sequence set forth in SEQ ID NO: 5.

10. The one-pot method according to claim 1, wherein the (R)-selective amino acid transaminase is an enzyme derived from *Escherichia coli* and encoded by the nucleic acid sequence set forth in SEQ ID NO: 6.

* * * * *

SEQUENCE LISTING

<160> NUMBER OF SEQ ID NOS: 13

<210> SEQ ID NO 1
<211> LENGTH: 1371
<212> TYPE: DNA
<213> ORGANISM: Ochrobactrumanthropi

<400> SEQUENCE: 1

```
atgactgctc agccaaactc tcttgaagct cgcgatatcc gttatcatct ccattcttat      60
accgatgctg tccgcctcga agcggaaggt ccgctcgtca tcgagcgtgg cgatggcatt     120
tacgtcgaag atgtatcggg caagcgctat atcgaagcga tgtcaggact gtggagtgtt     180
ggcgtgggct tttccgaacc gcgtctggcc gaagcagctg cacgacagat gaagaagctg     240
cctttctacc atacattctc ctaccgttcg catggtcctg tcattgatct ggcagaaaag     300
cttgtctcaa tggctcctgt tccgatgagc aaggcctact tcaccaattc aggttccgaa     360
gccaacgata cggtcgtcaa gttgatctgg tatcgctcca atgcgctggg tgaaccggag     420
cgcaagaaaa tcatctcacg caagcgcggc tatcacggtg tgacgattgc ctctgccagc     480
ctgaccggct tgcccaacaa tcaccgttct ttcgatctgc cgatcgatcg tatcctgcat     540
acgggctgcc cgcattttta tcgcgaagga caggctggcg agagtgagga acaattcgca     600
acgcggctgg cggatgagct ggaacagttg atcatcgcgg aaggtcctca caccatcgct     660
gctttcattg gcgagccggt gatgggggct ggcggcgtag tcgtgccgcc caaaacctat     720
tgggaaaaag tgcaggctgt tctcaagcgc tacgatattc tgctgatcgc cgacgaggtt     780
atttgcggct tcggacggac aggcaatctg ttcggcagcc agactttcga tatgaaaccg     840
gacattctgg tgatgtcgaa gcagctttcg tcatcctatc tgccgatttc ggccttcctc     900
atcaacgagc gtgtgtacgc gccaattgcc gaagaaagcc acaagatcgg cacgcttggc     960
acgggcttca cggcatctgg ccatccggtg gcggcagcgg tagcgctgga aaacctcgcc    1020
attattgaag agcgtgatct ggtcgccaat gcgcgcgacc gcggcaccta tatgcagaag    1080
cgcctgcgtg agttgcagga tcatcctctg gtcggcgaag tgcgtggcgt tggtctcata    1140
gccggtgtcg agcttgtcac cgacaagcag gccaagacgg gccttgaacc aaccggcgct    1200
ctgggcgcaa aggcaaacgc cgttcttcag gagcgcggcg tcatttcccg cgcaatgggc    1260
gatacgcttg ccttctgccc gccgctcatc atcaacgatc agcaggttga tacgatggtg    1320
tccgcgctcg aggcgacgct gaacgatgtt caggcaagcc tcaccaggta a             1371
```

<210> SEQ ID NO 2
<211> LENGTH: 1362
<212> TYPE: DNA
<213> ORGANISM: Paracoccusdenitrificans

<400> SEQUENCE: 2

```
atgaaccaac cgcaaagctg ggaagcccgg gccgagacct attcgctcta cggtttcacc      60
gacatgccct cggtccatca gcggggcacg gtcgtcgtga cccatggcga ggggccctat     120
atcgtcgatg tccatggccg ccgctatctg gatgccaatt cgggcctgtg aacatggtc     180
gcgggcttcg accacaaggg cctgatcgag gccgccaagg cgcaatacga ccgctttccc     240
ggctatcacg cctttttcgg ccgcatgtcc gaccagaccc tgatgctgtc ggaaaagctg     300
gtcgaggtct cgccattcga caacggccgg gtcttctata ccaattccgg ctccgaggcg     360
aacgacacca tggtcaagat gctgtggttc ctgcatgccg ccgagggcaa gccgcaaaag     420
cgcaagatcc tgacgcgctg gaacgcctat cacggcgtga ccgcggtttc ggcctcgatg     480
accggcaagc cctacaactc ggtcttcggc ctgccgctgc ccggcttcat ccacctgacc     540
tgcccgcatt actggcgcta tggcgaggaa ggcgagaccg aggcgcaatt cgtcgcccgc     600
ctggcacgcg agcttgagga taccatcacc cgcgagggcg ccgacaccat cgccggcttc     660
ttcgccgagc cggtgatggg cgcggggggg gtgatcccgc cggcgaaggg ttatttccag     720
gccatcctgc cgatcttgcg caagtatgac atcccgatga tctcggacga ggtgatctgc     780
ggcttcgggc gcaccggcaa cacctggggc tgcctgacct acgacttcat gcccgatgcg     840
atcatctcgt ccaagaacct gactgcgggc ttcttcccga tgggcgccgt catcctcggg     900
cccgacctcg ccaagcgggt cgaggccgcg gtcgaggcga tcgaggagtt cccgcacggc     960
ttcaccgcct cgggccatcc ggtcggctgc gccatcgcgc tgaaggccat cgacgtggtg    1020
atgaacgagg ggctggccga aatgtccgc cgcctcgcac cccgcttcga ggcggggctg    1080
aagcgcatcg ccgaccgccc gaacatcggc gaataccgcg gcatcggctt catgtgggcg    1140
ctggaggcgg tcaaggacaa gccgaccaag acccccttcg acgccaatct ttcggtcagc    1200
gagcgcatcg ccaatacctg caccgatctg gggctgatct gccggccgct gggccagtcc    1260
atcgtgctgt gcccgcccct tcatcctgacc gaggcgcaga tggacgagat gttcgaaaag    1320
ctggaaaagg cgctcgacaa ggtctttgcc gaggtggcct ga                       1362
```

<210> SEQ ID NO 3
<211> LENGTH: 978
<212> TYPE: DNA
<213> ORGANISM: Aspergillus terreus

<400> SEQUENCE: 3

```
atggcctcca tggacaaagt ctttgccggc tacgccgccc gccaagcgat cctcgaatca      60
accgagacca ccaacccctt tgcgaagggt atcgcctggg tagaaggcga gctggtgccc     120
ctggcagagg cacgcattcc actgctcgac cagggcttca tgcacagcga tctcacctac     180
gacgtgccct ccgtctggga cggccgcttc ttccggctag acgaccacat cacgcggctc     240
gaagccagct gcaccaagct ccggctgcga ctgccactcc cgcgcgacca ggtcaagcag     300
attctcgtcg agatggtggc caagagcggc atccgcgacg cctttgtcga gctgatcgtg     360
acgcgcgggc tgaagggcgt gcgggggaca cgccccgagg acatcgtcaa caatctgtac     420
atgtttgtgc agccgtacgt gtgggtgatg agccggata tgcagcgtgt cggcggcagc     480
gcggtcgtcg cccgcaccgt gcgccgggtg ccccgggtg ccatcgaccc aaccgtcaag     540
aacctgcaat gggcgatct cgtgcgcggc atgttcgagg ctgcggatcg cggtgcaact     600
tatccgttct tgacggacgg agatgcccat ctcaccgaag gctctggggtt caatattgtg     660
```

```
ctcgtcaagg acggcgtgct gtacacacca gaccgtggtg tgctgcaggg cgtgacacga    720
aagagtgtta tcaatgcggc ggaagccttc gggattgaag tccgcgttga gtttgtgccg    780
gttgagctgg cgtaccgttg tgatgagatc tttatgtgta ccaccgctgg cggcatcatg    840
cctatcacta cgctggatgg gatgcccgtg aatggaggac agatcggtcc tattacgaag    900
aagatttggg atggatattg ggctatgcat tatgatgcgg cttacagctt cgagattgat    960
tataacgaga ggaactga                                                  978

<210> SEQ ID NO 4
<211> LENGTH: 993
<212> TYPE: DNA
<213> ORGANISM: Arthrobacter sp.

<400> SEQUENCE: 4
atggcattta gcgcagatac accggaaatt gtttataccc atgataccgg tctggattat     60
attacctata gcgattatga actggatccg gcaaatccgc tggcaggcgg tgcagcatgg    120
attgaaggtg catttgttcc tccgagcgaa gcacgtatta gcattttga tcagggcttt    180 tataccagtg atgcaaccta taccaccttt catgtgtgga atggtaatgc atttcgtctg    240
ggtgatcata ttgaacgtct gtttagcaat gccgaaagca ttcgtctgat tcctccgctg    300
acccaggatg aagttaaaga aattgcactg gaactggttg caaaaaccga actgcgtgaa    360
gcaatggtta ccgttaccat tacccgtggt tatagcagca ccccgtttga acgtgatatt    420
accaaacatc gtccgcaggt ttatatgagc gcatgtccgt atcagtggat tgttccgttt    480
gatcgtattc gtgatggtgt tcatctgatg gttgcacaga gcgttcgtcg tacaccgcgt    540
agcagcattg atccgcaggt taaaaatttt cagtggggtg atctgattcg tgcaattcag    600
gaaacccacg atcgcggttt tgaactgccg ctgctgctgg attgtgataa tctgctggcc    660
gaaggtccgg gttttaatgt tgttgttatt aaagatggcg tggttcgtag tccgggtcgt    720
gcagcactgc ctggtattac ccgtaaaaac gttctggaaa ttgcagaaag cctgggtcat    780
gaagcaattc tggcagatat tacaccggca gaactgtatg atgcagatga agttctgggt    840
tgtagcaccg tggtggtgt ttggccgttt gttagcgttg atggtaatag cattagtgat    900
ggcgttccgg gtccgattac ccagagcatt attcgtcgtt attgggaact gaatgttgaa    960
ccgagcagcc tgctgacacc ggttcagtat tga                                 993

<210> SEQ ID NO 5
<211> LENGTH: 852
<212> TYPE: DNA
<213> ORGANISM: Bacillus sp.

<400> SEQUENCE: 5
atggcatact cattatggaa tgaccaaatc gttgaagaag gatctattac aatttcacca     60
gaagaccgtg gttatcaatt tggtgatggt atttacgaag taatcaaagt atataacggg    120 catatgtttta cagcacaaga gcacatcgat cgtttctatg ctagtgccga aaaaattcgc    180
cttgttattc cttatacaaa agatgtatta cacaaattat tgcatgattt aatcgaaaaa    240
aataatttaa atacaggtca tgtttacttc caaattacac gtggaacaac ttctcgtaac    300
cacattttcc cggatgcaag cgtaccagca gtgctaacag gtaatgttaa aactggtgaa    360
cgttcaattg aaaatttcga aaaggcgta aaagcgacat tggttgaaga tgttcgttgg    420
ttacgttgtg atattaaatc tttaaatta cttggcgcgg tacttgcgaa acaagaagca    480
tctgaaaaag gttgttacga agccatttta caccgtggag atattatcac agaatgttct    540
```

| tctgctaatg tctatggtat taaagatggt aaactttata cgcacccagc aaataactac | 600 |
| atcttaaatg gtattacacg ccaagttata ttaaaatgtg ccgctgaaat aaatttacca | 660 |
| gtgattgaag agccgatgac aaaaggcgat ttattaacaa tggatgaaat tattgtgtct | 720 |
| tctgtttcat ctgaagtgac accggttatc gatgtggatg gtcagcaaat tggtgcaggt | 780 |
| gttcctggtg aatggactcg taaattgcaa aaagcatttg aggcaaaatt accaatttca | 840 |
| attaatgcct aa | 852 |

```
<210> SEQ ID NO 6
<211> LENGTH: 930
<212> TYPE: DNA
<213> ORGANISM: Escherichia coli

<400> SEQUENCE: 6
```

| atgaccacga agaaagctga ttacattttgg ttcaatgggg agatggttcg ctgggaagac | 60 |
| gcgaaggtgc atgtgatgtc gcacgcgctg cactatggca cttcggtttt tgaaggcatc | 120 |
| cgttgctacg actcgcacaa aggaccggtt gtattccgcc atcgtgagca tatgcagcgt | 180 |
| ctgcatgact ccgccaaaat ctatcgcttc ccggtttcgc agagcattga tgagctgatg | 240 |
| gaagcttgtc gtgacgtgat ccgcaaaaac aatctcacca gcgcctatat ccgtccgctg | 300 |
| atcttcgtcg gtgatgttgg catgggagta aacccgccag cgggatactc aaccgacgtg | 360 |
| attatcgctg ctttcccgtg gggagcgtat ctgggcgcag aagcgctgga gcaggggatc | 420 |
| gatgcgatgg tttcctcctg gaaccgcgca gcaccaaaca ccatcccgac ggcggcaaaa | 480 |
| gccggtggta actacctctc ttccctgctg gtgggtagcg aagcgcgccg ccacggttat | 540 |
| caggaaggta tcgcgctgga tgtgaacggt tatatctctg aaggcgcagg cgaaaacctg | 600 |
| tttgaagtga agatggtgt gctgttcacc ccaccgttca cctcctccgc gctgccgggt | 660 |
| attacccgtg atgccatcat caaactggcg aaagagctgg gaattgaagt acgtgagcag | 720 |
| gtgctgtcgc gcgaatccct gtacctggcg gatgaagtgt ttatgtccgg tacggcggca | 780 |
| gaaatcacgc cagtgcgcag cgtagacggt attcaggttg gcgaaggccg ttgtggcccg | 840 |
| gttaccaaac gcattcagca agccttcttc ggcctcttca ctggcgaaac cgaagataaa | 900 |
| tggggctggt tagatcaagt taatcaataa | 930 |

```
<210> SEQ ID NO 7
<211> LENGTH: 1545
<212> TYPE: DNA
<213> ORGANISM: Escherichia coli

<400> SEQUENCE: 7
```

| atggctgact cgcaacccct gtccggtgct ccggaaggtg ccgaatattt aagagcagtg | 60 |
| ctgcgcgcgc cggtttacga ggcggcgcag gttacgccgc tacaaaaaat ggaaaaactg | 120 |
| tcgtcgcgtc ttgataacgt cattctggtg aagcgcgaag atcgccagcc agtgcacagc | 180 |
| tttaagctgc gcggcgcata cgccatgatg gcgggcctga cggaagaaca gaaagcgcac | 240 |
| ggcgtgatca ctgcttctgc gggtaaccac gcgcagggcg tcgcgttttc ttctgcgcgg | 300 |
| ttaggcgtga aggccctgat cgttatgcca accgccaccg ccgacatcaa agtcgacgcg | 360 |
| gtgcgcggct tcggcggcga agtgctgctc cacggcgcga actttgatga agcgaaagcc | 420 |
| aaagcgatcg aactgtcaca gcagcagggg ttcacctggg tgccgccgtt cgaccatccg | 480 |
| atggtgattg ccgggcaagg cacgctggcg ctggaactgc tccagcagga cgcccatctc | 540 |

```
gaccgcgtat ttgtgccagt cggcggcggc ggtctggctg ctggcgtggc ggtgctgatc    600
aaacaactga tgccgcaaat caaagtgatc gccgtagaag cggaagactc cgcctgcctg    660
aaagcagcgc tgaatgcggg tcatccggtt gatctgccgc gcgtagggct atttgctgaa    720
ggcgtagcgg taaaacgcat cggtgacgaa accttccgtt tatgccagga gtatctcgac    780
gacatcatca ccgtcgatag cgatgcgatc tgtgcggcga tgaaggattt attcgaagat    840
gtgcgcgcgg tggcggaacc ctctggcgcg ctggcgctgg cgggaatgaa aaaatatatc    900
gccctgcaca acattcgcgg cgaacggctg gcgcatattc tttccggtgc caacgtgaac    960
ttccacggcc tgcgctacgt ctcagaacgc tgcgaactgg cgaacagcg tgaagcgttg    1020 ttggcggtga ccattccgga agaaaaaggc agcttcctca aattctgcca actgcttggc    1080
gggcgttcgg tcaccgagtt caactaccgt tttgccgatg ccaaaaacgc ctgcatcttt    1140
gtcggtgtgc gcctgagccg cggcctcgaa gagcgcaaag aaattttgca gatgctcaac    1200
gacggcggct acagcgtggt tgatctctcc gacgacgaaa tggcgaagct acacgtgcgc    1260
tatatggtcg gcggacgtcc atcgcatccg ttgcaggaac gcctctacag cttcgaattc    1320
ccggaatcac cgggcgcgct gctgcgcttc ctcaacacgc tgggtacgta ctggaacatt    1380
tctttgttcc actatcgcag ccatggcacc gactacgggc gcgtactggc ggcgttcgaa    1440
cttggcgacc atgaaccgga tttcgaaacc cggctgaatg agctgggcta cgattgccac    1500
gacgaaacca taacccggc gttcaggttc ttttggcgg gttaa                      1545
```

<210> SEQ ID NO 8
<211> LENGTH: 456
<212> TYPE: PRT
<213> ORGANISM: Ochrobactrum anthropi

<400> SEQUENCE: 8

Met Thr Ala Gln Pro Asn Ser Leu Glu Ala Arg Asp Ile Arg Tyr His
  1               5                  10                  15

Leu His Ser Tyr Thr Asp Ala Val Arg Leu Glu Ala Glu Gly Pro Leu
                 20                  25                  30

Val Ile Glu Arg Gly Asp Gly Ile Tyr Val Glu Asp Val Ser Gly Lys
             35                  40                  45

Arg Tyr Ile Glu Ala Met Ser Gly Leu Trp Ser Val Gly Val Gly Phe
         50                  55                  60

Ser Glu Pro Arg Leu Ala Glu Ala Ala Ala Arg Gln Met Lys Lys Leu
65                  70                  75                  80

Pro Phe Tyr His Thr Phe Ser Tyr Arg Ser His Gly Pro Val Ile Asp
                 85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu

```
                195                 200                 205
Gln Leu Ile Ile Ala Glu Gly Pro His Thr Ile Ala Ala Phe Ile Gly
    210                 215                 220

Glu Pro Val Met Gly Ala Gly Val Val Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 9
<211> LENGTH: 453
<212> TYPE: PRT
<213> ORGANISM: Paracoccusdenitrificans

<400> SEQUENCE: 9

Met Asn Gln Pro Gln Ser Trp Glu Ala Arg Ala Glu Thr Tyr Ser Leu
1               5                   10                  15

Tyr Gly Phe Thr Asp Met Pro Ser Val His Gln Arg Gly Thr Val Val
                20                  25                  30

Val Thr His Gly Glu Gly Pro Tyr Ile Val Asp Val His Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Glu Ala Lys Ala Gln Tyr Asp Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Asn Gly Arg Val Phe
            100                 105                 110
```

```
Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Ile His Leu Thr Cys Pro His Tyr Trp Arg Tyr Gly Glu Glu Gly Glu
            180                 185                 190

Thr Glu Ala Gln Phe Val Ala Arg Leu Ala Arg Glu Leu Glu Asp Thr
            195                 200                 205

Ile Thr Arg Glu Gly Ala Asp Thr Ile Ala Gly Phe Phe Ala Glu Pro
            210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Met Ile Ser Asp
                245                 250                 255

Glu Val Ile Cys Gly Phe Gly Arg Thr Gly Asn Thr Trp Gly Cys Leu
            260                 265                 270

Thr Tyr Asp Phe Met Pro Asp Ala Ile Ile Ser Ser Lys Asn Leu Thr
            275                 280                 285

Ala Gly Phe Phe Pro Met Gly Ala Val Ile Leu Gly Pro Asp Leu Ala
            290                 295                 300

Lys Arg Val Glu Ala Ala Val Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Ala Gly Leu Lys Arg Ile Ala Asp Arg Pro Asn
            355                 360                 365

Ile Gly Glu Tyr Arg Gly Ile Gly Phe Met Trp Ala Leu Glu Ala Val
            370                 375                 380

Lys Asp Lys Pro Thr Lys Thr Pro Phe Asp Ala Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Ile Val Leu Cys Pro Pro Phe Ile Leu Thr Glu Ala
            420                 425                 430

Gln Met Asp Glu Met Phe Glu Lys Leu Glu Lys Ala Leu Asp Lys Val
            435                 440                 445

Phe Ala Glu Val Ala
    450

<210> SEQ ID NO 10
<211> LENGTH: 283
<212> TYPE: PRT
<213> ORGANISM: Bacillus sphaericus

<400> SEQUENCE: 10

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
            20                  25                  30
```

Glu Val Ile Lys Val Tyr Asn Gly His Met Phe Thr Ala Gln Glu His
 35                  40                  45

Ile Asp Arg Phe Tyr Ala Ser Ala Glu Lys Ile Arg Leu Val Ile Pro
 50                  55                  60

Tyr Thr Lys Asp Val Leu His Lys Leu His Asp Leu Ile Glu Lys
 65              70                  75                  80

Asn Asn Leu Asn Thr Gly His Val Tyr Phe Gln Ile Thr Arg Gly Thr
                 85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
            115                 120                 125

Gly Val Lys Ala Thr Leu Val Glu Asp Val Arg Trp Leu Arg Cys Asp
130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
            180                 185                 190

Tyr Thr His Pro Ala Asn Asn Tyr Ile Leu Asn Gly Ile Thr Arg Gln
            195                 200                 205

Val Ile Leu Lys Cys Ala Ala Glu Ile Asn Leu Pro Val Ile Glu Glu
210                 215                 220

Pro Met Thr Lys Gly Asp Leu Leu Thr Met Asp Glu Ile Val Ser
225                 230                 235                 240

Ser Val Ser Ser Glu Val Thr Pro Val Ile Asp Val Asp Gly Gln Gln
                245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
            275                 280

<210> SEQ ID NO 11
<211> LENGTH: 325
<212> TYPE: PRT
<213> ORGANISM: Aspergillus terreus

<400> SEQUENCE: 11

Met Ala Ser Met Asp Lys Val Phe Ala Gly Tyr Ala Ala Arg Gln Ala
 1               5                  10                  15

Ile Leu Glu Ser Thr Glu Thr Thr Asn Pro Phe Ala Lys Gly Ile Ala
                 20                  25                  30

Trp Val Glu Gly Glu Leu Val Pro Leu Ala Glu Ala Arg Ile Pro Leu
             35                  40                  45

Leu Asp Gln Gly Phe Met His Ser Asp Leu Thr Tyr Asp Val Pro Ser
         50                  55                  60

Val Trp Asp Gly Arg Phe Phe Arg Leu Asp Asp His Ile Thr Arg Leu
 65                  70                  75                  80

Glu Ala Ser Cys Thr Lys Leu Arg Leu Arg Leu Pro Leu Pro Arg Asp
                 85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg

-continued

```
            115                 120                 125
Gly Thr Arg Pro Glu Asp Ile Val Asn Asn Leu Tyr Met Phe Val Gln
130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
                180                 185                 190

Glu Ala Ala Asp Arg Gly Ala Thr Tyr Pro Phe Leu Thr Asp Gly Asp
                195                 200                 205

Ala His Leu Thr Glu Gly Ser Gly Phe Asn Ile Val Leu Val Lys Asp
                210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255

Glu Phe Val Pro Val Glu Leu Ala Tyr Arg Cys Asp Glu Ile Phe Met
                260                 265                 270

Cys Thr Thr Ala Gly Gly Ile Met Pro Ile Thr Thr Leu Asp Gly Met
                275                 280                 285

Pro Val Asn Gly Gly Gln Ile Gly Pro Ile Thr Lys Lys Ile Trp Asp
                290                 295                 300

Gly Tyr Trp Ala Met His Tyr Asp Ala Ala Tyr Ser Phe Glu Ile Asp
305                 310                 315                 320

Tyr Asn Glu Arg Asn
                325

<210> SEQ ID NO 12
<211> LENGTH: 514
<212> TYPE: PRT
<213> ORGANISM: Escherichia coli

<400> SEQUENCE: 12

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
                20                  25                  30

Pro Leu Gln Lys Met Glu Lys Leu Ser Ser Arg Leu Asp Asn Val Ile
                35                  40                  45

Leu Val Lys Arg Glu Asp Arg Gln Pro Val His Ser Phe Lys Leu Arg
50                  55                  60

Gly Ala Tyr Ala Met Met Ala Gly Leu Thr Glu Glu Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
                100                 105                 110

Thr Ala Asp Ile Lys Val Asp Ala Val Arg Gly Phe Gly Gly Glu Val
                115                 120                 125

Leu Leu His Gly Ala Asn Phe Asp Glu Ala Lys Ala Lys Ala Ile Glu
                130                 135                 140

Leu Ser Gln Gln Gln Gly Phe Thr Trp Val Pro Pro Phe Asp His Pro
145                 150                 155                 160
```

```
Met Val Ile Ala Gly Gln Gly Thr Leu Ala Leu Glu Leu Leu Gln Gln
                165                 170                 175
Asp Ala His Leu Asp Arg Val Phe Val Pro Val Gly Gly Gly Gly Leu
            180                 185                 190
Ala Ala Gly Val Ala Val Leu Ile Lys Gln Leu Met Pro Gln Ile Lys
        195                 200                 205
Val Ile Ala Val Glu Ala Glu Asp Ser Ala Cys Leu Lys Ala Ala Leu
    210                 215                 220
Asn Ala Gly His Pro Val Asp Leu Pro Arg Val Gly Leu Phe Ala Glu
225                 230                 235                 240
Gly Val Ala Val Lys Arg Ile Gly Asp Glu Thr Phe Arg Leu Cys Gln
                245                 250                 255
Glu Tyr Leu Asp Asp Ile Ile Thr Val Asp Ser Asp Ala Ile Cys Ala
            260                 265                 270
Ala Met Lys Asp Leu Phe Glu Asp Val Arg Ala Val Ala Glu Pro Ser
        275                 280                 285
Gly Ala Leu Ala Leu Ala Gly Met Lys Lys Tyr Ile Ala Leu His Asn
    290                 295                 300
Ile Arg Gly Glu Arg Leu Ala His Ile Leu Ser Gly Ala Asn Val Asn
305                 310                 315                 320
Phe His Gly Leu Arg Tyr Val Ser Glu Arg Cys Glu Leu Gly Glu Gln
                325                 330                 335
Arg Glu Ala Leu Leu Ala Val Thr Ile Pro Glu Glu Lys Gly Ser Phe
            340                 345                 350
Leu Lys Phe Cys Gln Leu Leu Gly Gly Arg Ser Val Thr Glu Phe Asn
        355                 360                 365
Tyr Arg Phe Ala Asp Ala Lys Asn Ala Cys Ile Phe Val Gly Val Arg
    370                 375                 380
Leu Ser Arg Gly Leu Glu Glu Arg Lys Glu Ile Leu Gln Met Leu Asn
385                 390                 395                 400
Asp Gly Gly Tyr Ser Val Val Asp Leu Ser Asp Asp Glu Met Ala Lys
                405                 410                 415
Leu His Val Arg Tyr Met Val Gly Gly Arg Pro Ser His Pro Leu Gln
            420                 425                 430
Glu Arg Leu Tyr Ser Phe Glu Phe Pro Glu Ser Pro Gly Ala Leu Leu
        435                 440                 445
Arg Phe Leu Asn Thr Leu Gly Thr Tyr Trp Asn Ile Ser Leu Phe His
    450                 455                 460
Tyr Arg Ser His Gly Thr Asp Tyr Gly Arg Val Leu Ala Ala Phe Glu
465                 470                 475                 480
Leu Gly Asp His Glu Pro Asp Phe Glu Thr Arg Leu Asn Glu Leu Gly
                485                 490                 495
Tyr Asp Cys His Asp Glu Thr Asn Asn Pro Ala Phe Arg Phe Phe Leu
            500                 505                 510
Ala Gly

<210> SEQ ID NO 13
<211> LENGTH: 309
<212> TYPE: PRT
<213> ORGANISM: Escherichia coli

<400> SEQUENCE: 13

Met Thr Thr Lys Lys Ala Asp Tyr Ile Trp Phe Asn Gly Glu Met Val
1               5                   10                  15
```

```
Arg Trp Glu Asp Ala Lys Val His Val Met Ser His Ala Leu His Tyr
             20                  25                  30
Gly Thr Ser Val Phe Glu Gly Ile Arg Cys Tyr Asp Ser His Lys Gly
         35                  40                  45
Pro Val Val Phe Arg His Arg Glu His Met Gln Arg Leu His Asp Ser
     50                  55                  60
Ala Lys Ile Tyr Arg Phe Pro Val Ser Gln Ser Ile Asp Glu Leu Met
 65              70                  75                      80
Glu Ala Cys Arg Asp Val Ile Arg Lys Asn Asn Leu Thr Ser Ala Tyr
                 85                  90                  95
Ile Arg Pro Leu Ile Phe Val Gly Asp Val Gly Met Gly Val Asn Pro
             100                 105                 110
Pro Ala Gly Tyr Ser Thr Asp Val Ile Ile Ala Ala Phe Pro Trp Gly
             115                 120                 125
Ala Tyr Leu Gly Ala Glu Ala Leu Glu Gln Gly Ile Asp Ala Met Val
130                 135                 140
Ser Ser Trp Asn Arg Ala Ala Pro Asn Thr Ile Pro Thr Ala Ala Lys
145                 150                 155                 160
Ala Gly Gly Asn Tyr Leu Ser Ser Leu Leu Val Gly Ser Glu Ala Arg
                 165                 170                 175
Arg His Gly Tyr Gln Glu Gly Ile Ala Leu Asp Val Asn Gly Tyr Ile
             180                 185                 190
Ser Glu Gly Ala Gly Glu Asn Leu Phe Glu Val Lys Asp Gly Val Leu
             195                 200                 205
Phe Thr Pro Pro Phe Thr Ser Ser Ala Leu Pro Gly Ile Thr Arg Asp
     210                 215                 220
Ala Ile Ile Lys Leu Ala Lys Glu Leu Gly Ile Glu Val Arg Glu Gln
225                 230                 235                 240
Val Leu Ser Arg Glu Ser Leu Tyr Leu Ala Asp Glu Val Phe Met Ser
                 245                 250                 255
Gly Thr Ala Ala Glu Ile Thr Pro Val Arg Ser Val Asp Gly Ile Gln
             260                 265                 270
Val Gly Glu Gly Arg Cys Gly Pro Val Thr Lys Arg Ile Gln Gln Ala
             275                 280                 285
Phe Phe Gly Leu Phe Thr Gly Glu Thr Glu Asp Lys Trp Gly Trp Leu
     290                 295                 300
Asp Gln Val Asn Gln
305
```